(12) United States Patent
Romero-Ortega et al.

(10) Patent No.: US 10,646,617 B2
(45) Date of Patent: May 12, 2020

(54) CHEMICAL GRADIENTS

(71) Applicant: BOARD OF REGENTS, THE UNIVERSITY OF TEXAS SYSTEM, Austin, TX (US)

(72) Inventors: Mario I. Romero-Ortega, Coppell, TX (US); Parisa Lotfi, Houston, TX (US); Benjamin R. Johnston, Arlington, TX (US); Swarupnarayan Dash, Arlington, TX (US); Joselito Razal, Wollongong (AU); Gordon Wallace, Wollongong (AU)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/911,738

(22) Filed: Mar. 5, 2018

(65) Prior Publication Data

US 2018/0193521 A1    Jul. 12, 2018

Related U.S. Application Data

(63) Continuation of application No. 14/768,820, filed as application No. PCT/US2014/016905 on Feb. 18, 2014, now Pat. No. 9,931,432.

(60) Provisional application No. 61/766,366, filed on Feb. 19, 2013.

(51) Int. Cl.
*A61L 27/18* (2006.01)
*A61L 27/20* (2006.01)
*A61L 27/54* (2006.01)
*A61L 27/58* (2006.01)

(52) U.S. Cl.
CPC ............... *A61L 27/18* (2013.01); *A61L 27/20* (2013.01); *A61L 27/54* (2013.01); *A61L 27/58* (2013.01); *A61L 2430/32* (2013.01)

(58) Field of Classification Search
None
See application file for complete search history.

(56) References Cited

U.S. PATENT DOCUMENTS 4,749,576 A * 6/1988 Lee ..................... A61K 9/2027
424/486

* cited by examiner

*Primary Examiner* — Brian Gulledge
(74) *Attorney, Agent, or Firm* — Christopher S. Dodson; Nexsen Pruet, PLLC

(57) ABSTRACT

In one aspect, apparatuses for providing chemical gradients are described herein. In some embodiments, an apparatus described herein comprises a conduit having a first end and a second end, one or more microchannels disposed in the conduit and extending from the first end toward the second end, and a fiber coiled around the exterior of at least one microchannel, wherein the fiber comprises an active agent that is operable to diffuse into the interior of the microchannel.

13 Claims, 17 Drawing Sheets

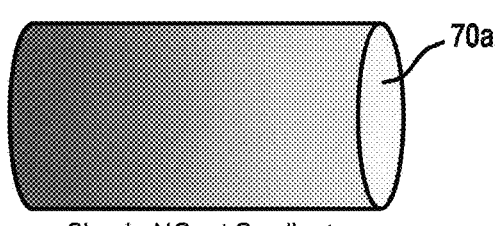
Simple NG w/ Gradient
FIG. 7A
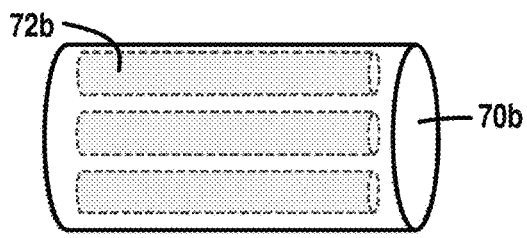
Multiluminal NG
FIG. 7B
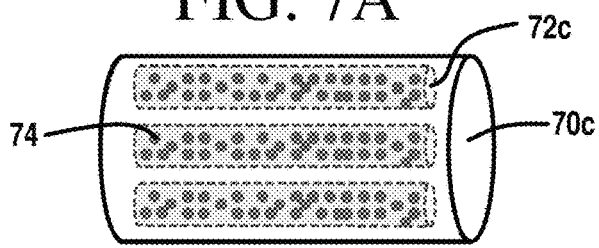
Multiluminal NG w/Uniform NTF
FIG. 7C
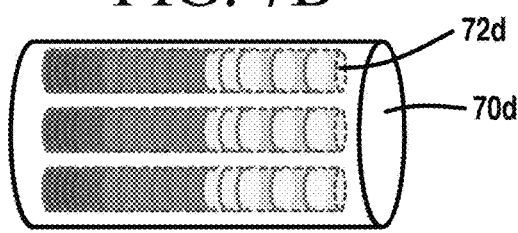
Multiluminal NG w/ Gradient
FIG. 7D
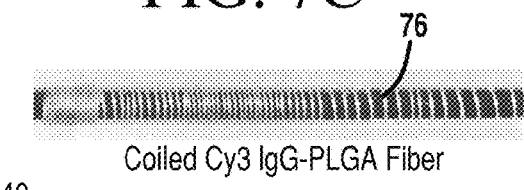
Coiled Cy3 IgG-PLGA Fiber
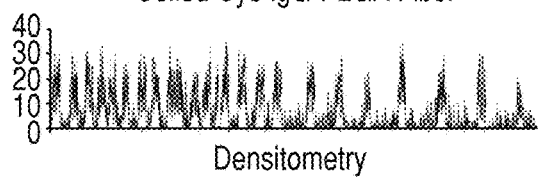
Densitometry
FIG. 7E
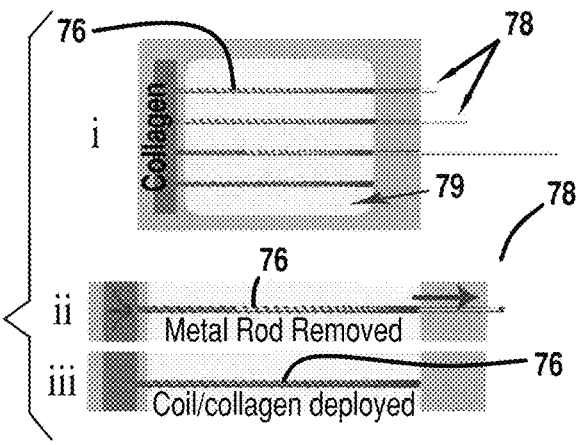
FIG. 7F
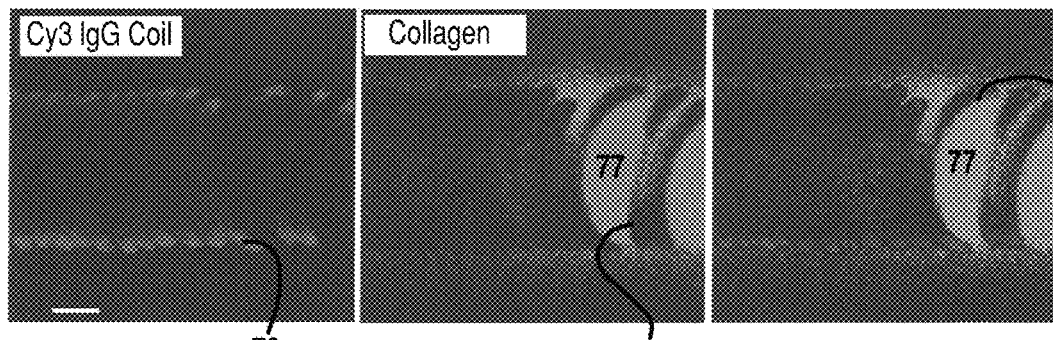
FIG. 7G  FIG. 7H  FIG. 7I

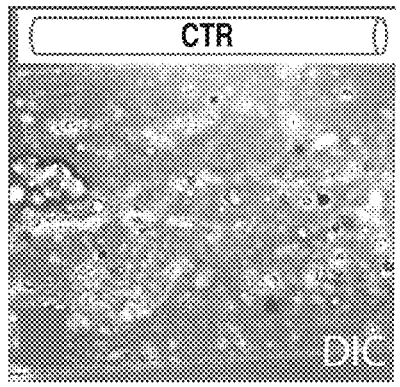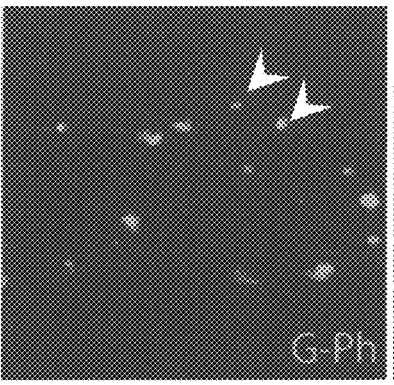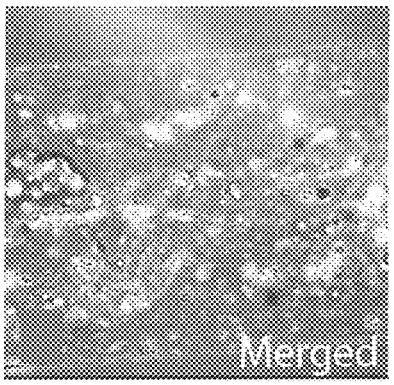
FIG. 10A             FIG. 10B             FIG. 10C
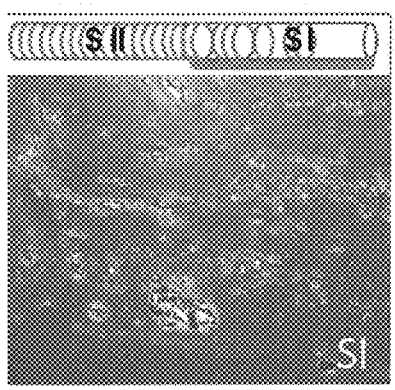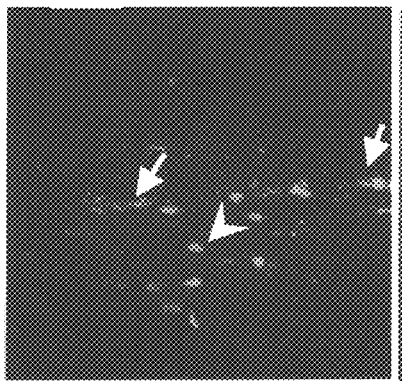
FIG. 10D             FIG. 10E             FIG. 10F
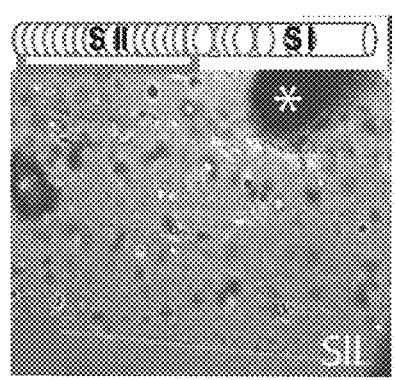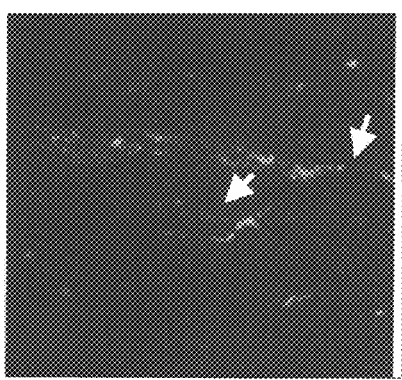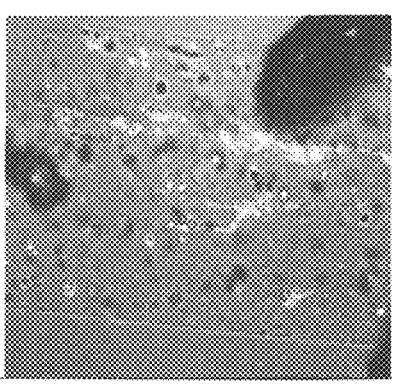
FIG. 10G             FIG. 10H             FIG. 10I

CHEMICAL GRADIENTS

CROSS REFERENCE TO RELATED APPLICATION

This application is a continuation of U.S. patent application Ser. No. 14/768,820, filed Aug. 19, 2015, which is a National Stage Application under 35 U.S.C. § 371 of International Patent Application No. PCT/US2014/016905, filed Feb. 18, 2014, which claims priority pursuant to 35 U.S.C. § 119(e) to U.S. Provisional Patent Application No. 61/766,366, filed on Feb. 19, 2013, each of which is hereby incorporated by reference in its entirety.

STATEMENT REGARDING FEDERALLY SPONSORED RESEARCH

This invention was made with government support under grant 1R21Ns072955-01A1 awarded by the National Institutes of Health/National Institute of Neurological Disorders and Stroke (NIH/NINDS).

FIELD

This invention relates to apparatuses and methods for forming chemical gradients and compositions comprising chemical gradients and, in particular, to chemical gradients for drug delivery and other biomedical applications.

BACKGROUND

During development and after injury, neural cells migrate and elongate their axons towards proper target cells and organs in response to gradients of biomolecules, which guide axonal regeneration (chemotaxis) either by attachment to the cells or to the extracellular matrix (ECM), or by secretion into the extracellular fluid. In some cases, chemotactic soluble molecules are secreted by specific cells, and gradients are formed through diffusion and convection from the site of release. Cellular responses to such gradients can be influenced by the nature of the biomolecules, and physical characteristics of the ECM (which can include collagen, fibronectin, and laminin), such as matrix pore size and stiffness. In the developing peripheral nervous system (PNS), gradients of neurotrophic factors (NTF) such as nerve growth factor (NGF), neurotrophin 3 (NT-3), and brain-derived neurotrophic factor (BDNF), are established by distal target cells and direct axonal elongation and target recognition of motor neurons (VMN) from the ventral spinal cord, as well as sensory neurons in the dorsal root ganglia (DRG). In the adult PNS, the efferent branch of sensory neurons re-innervates skin and muscle targets spontaneously after injury, but afferent axons are unable to enter the hostile environment of the adult spinal cord, unless enticed by induced NGF expression. Moreover, pathfinding errors made by injured VMN and DGR neurons during regeneration can be dramatically reduced by the expression of the appropriate gene expression that re-establishes NTF gradients.

Unfortunately, the creation of chemical gradients such as NTF gradients and the use of chemical gradients in nerve repair remain extremely challenging. For example, some prior technologies fail to provide sustained release of desired molecular signals and/or lack ECM support. Other technologies lack the ability to provide non-transient and/or physiologically relevant chemical gradients normally present in vivo. Further, some previous methods for creating a chemical gradient are applicable to only short-term studies in vitro and/or present risks associated with the injection of a viral vector. Therefore, improved apparatuses and methods for providing a chemical gradient are desired.

SUMMARY

The present disclosure relates to methods, apparatuses and compositions useful in tissue repair through establishing highly tunable chemical gradients such as NTF or NGF gradients designed to direct axonal growth through multiluminal or multichannel hydrogels filled with ECM. To that end, the present disclosure relates to a novel coiled polymeric structure anchored to the walls of hydrogel microchannels to establish highly and predictably regulated gradients of controllable and sustained NTF release that permeates the luminar collagen, which in turn stabilizes gradients of diffusible factors and provides permissive and predictably regulated and controlled/controllable growth substrates for axonal elongation. A mathematical model was determined to describe NTF diffusion in this complex matrix and to determine the luminal NTF concentration over time, using DRG in vitro neural growth assays to provide evidence of chemotactic nerve regeneration along the three-dimensional NGF gradients. This method is thought to prove beneficial for guided tissue repair, among other uses.

Aspects of the present disclosure are directed to apparatuses, comprising at least one conduit having a first end and a second end and one or more microchannels disposed in the conduit and extending from the first end toward the second end. A fiber is coiled around the exterior of at least one microchannel, wherein the fiber comprises an active agent that is operable to diffuse into the interior of the microchannel. In a further aspect, the conduit comprises catheter tubing such as Micro-Renathane implantation tubing.

In a still further aspect, the microchannels are disposed within a matrix material disposed in the conduit. Still further, the matrix material can comprise an agarose gel, a polylactic-co-glycolic acid (PLGA), polylactic acid (PLA), polycaprolactone, polyurethane, a polyester, polycarbonate, collagen, polytetrafluoroethylene (PTFE), polymethylmethacrylate (PMMA), an ethylene-vinylacetate copolymer (EVA), a polydimethylsiloxane (PDMS), polyether-polyurethane, a polyethyleneterephthalate (PET), a polysulfone (PS), a polyethyleneoxide (PEO) or polyethylene glycol (PEG), a polyethylene oxide-polypropylene oxide copolymer (PEO-PPO), a polyolefin such as polyethylene (PE) or polypropylene (PP), or a combination of one or more of the foregoing.

In yet another aspect, the matrix material comprises an agrarose gel comprising between about 1.5 weight percent and 2.5 weight percent agarose, based on the total weight of the agarose gel. Still further, a plurality of microchannels is preferably disposed in the conduit, and a plurality of fibers is coiled around the exteriors of a plurality of microchannels.

In a still further aspect, the plurality of fibers are each coiled around the exterior of a different microchannel, and at least two of the coiled fibers comprise differing active agents, differing amounts of an active agent, and/or differing pitches.

In yet another aspect, the fiber comprises or is formed from a polymeric material, such as, for example, a polylactic-co-glycolic acid, a polylactic acid, a caprolactone, or a combination thereof. A fiber can also comprise or be formed from other materials. Additionally, in a further aspect, the polymer is biodegradable.

In a still further variation, the fiber is coiled around the exterior of the microchannel in an isotropic configuration and/or an anisotropic configuration.

In another aspect, the active agent comprises a drug and/or a growth factor.

Aspects of the disclosure are further directed to methods of forming a chemical gradient comprising disposing any of the apparatuses described herein in a biological compartment. Further aspects contemplate that the biological compartment comprises a nerve conduit. Preferably, the active agent gradient comprises a drug gradient and/or a growth factor gradient.

Aspects of the present disclosure are also directed to a composition comprising a coiled polymeric material comprising an active agent operable to diffuse out of the polymeric material when the polymeric material is disposed in a biological compartment. In another aspect, the polymeric material preferably comprises a polylactic-co-glycolic acid, a polylactic acid, a caprolactone, or a combination thereof. In a still further aspect, the polymeric material is biodegradable. In yet another aspect, the active agent comprises a drug and/or growth factor. In a still further aspect, the biological compartment comprises a nerve conduit.

Further variations of the present disclosure are further directed to a composition, and apparatuses comprising a composition, that comprises a first gel comprising an active agent at a first concentration and a second gel comprising an active agent at a second concentration, wherein the first gel and the second gel are arranged in space to provide a concentration gradient of the active agent.

In a further aspect, the composition comprises a third gel comprising an active agent at a third concentration, the first gel, second gel, and third gel arranged in space, or oriented, to provide a gradient region comprising a concentration gradient of the active agent. In yet another aspect, the gradient region comprises a linear concentration gradient. Still further, the first, second, and third gels are arranged to provide a plurality of linear concentration gradients, or the first, second, and third gels are arranged or oriented in space to provide a non-gradient region in addition to the gradient region.

In another variation, the present disclosure is directed to a composition described above, wherein the first gel and/or the second gel comprises an agarose gel, a polylactic-co-glycolic acid, a polylactic acid, a caprolactone, or a combination thereof and the active agent comprises a drug or growth factor.

Still further, the present disclosure is directed to an apparatus comprising a conduit and any of the aforementioned compositions disposed in the conduit.

In addition, the present disclosure is directed to a method of forming a chemical or active agent concentration gradient comprising disposing any of the aforementioned apparatuses in a biological compartment, such as, for example a nerve conduit, and wherein the chemical or active agent concentration gradient comprises a drug gradient or a growth factor gradient.

Still further, the present disclosure is directed to a method for forming a chemical or active agent gradient comprising disposing any of the aforementioned compositions in a biological compartment, such as, for example, a nerve conduit, and wherein the chemical or active agent concentration gradient comprises a drug gradient or a growth factor gradient.

BRIEF DESCRIPTION OF THE DRAWINGS

FIG. 7A illustrates a schematic perspective view of a chemical gradient according to one embodiment described herein.

FIGS. 7B-C illustrate perspective views of conduits comprising a plurality of microchannels.

FIG. 7D illustrates a perspective view of an apparatus comprising a plurality of microchannels according to one embodiment described herein.

FIG. 7E illustrates a perspective view of an apparatus according to one embodiment described herein and the apparatus's corresponding densitometry profile.

FIGS. 7Fi-iii illustrate a process of making an apparatus according to embodiment described herein.

FIGS. 7G-I are microscope images of a aspect shown in FIG. 7E.

FIGS. 10A-I illustrate microscope images of nerve cells disposed in chemical gradients according to some embodiments described herein.

DETAILED DESCRIPTION

Figure 1A:
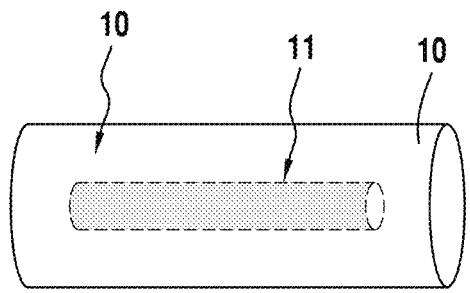
FIGS. 1A-B illustrate perspective views of conduits comprising a microchannel.

Aspects described herein can be understood more readily by reference to the following detailed description, examples, and figures. Elements, apparatus, and methods described herein, however, are not limited to the specific embodiments presented in the detailed description, examples, and figures. It should be recognized that disclosed embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all sub-ranges subsumed therein. For example, a stated range of "1.0 to 10.0" should be considered to include any and all sub-ranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

As described further hereinbelow, the present disclosure relates to methods, apparatuses, and compositions useful for forming chemical gradients, including within a biological environment. Further, such chemical gradients can be used for tissue repair and/or drug delivery. For example, in some cases, tissue repair can be achieved by establishing a highly tunable nerve growth factor (NGF) gradient designed to direct axonal growth through microchannels of an apparatus described herein, such as hydrogel microchannels filled with extracelluclar matrix (ECM) material.

Aspects of the present disclosure are, therefore, directed to apparatuses, methods, and compositions that can be used to provide a sustained chemical gradient, including in a biological environment. In one variation, fibers incorporating known amounts of active agents, such as growth factors, are coiled in a predetermined and preselected orientation, preferably about the walls, or outer circumference, of a microchannel in a conduit. In this way, the active ingredient can be controllably provided to a tissue introduced into the microchannel at a predetermined concentration. In some embodiments, the concentration of the active agent delivery can be predictably altered along the length of the microchannel by intentionally altering the fiber pitch or number of coils present in a given area along the length of the microchannel. In this manner, a concentration gradient along the length of the micochannel can be established. For example, when an active agent such as a growth factor (GF) is provided in the coiled fibers, such coiled fibers can be coiled or wrapped around, or inside of, one or more microchannels or lumens to provide one or more defined GF gradients in the microchannels or lumens. Therefore, methods, apparatuses, and compositions are disclosed to create a predetermined, preselected, and predictably controlled chemical gradient. Such a chemical gradient can also be referred to herein as a "programmable" gradient. In some embodiments, the gradient is accomplished by the pitch or number of turns of a fiber described herein.

An apparatus described herein, in some embodiments, comprises a conduit having a first end and a second end, one or more microchannels disposed in the conduit and extending from the first end toward the second end, and a fiber coiled around the exterior of at least one microchannel, wherein the fiber comprises an active agent that is operable to diffuse into the interior of the microchannel. The conduit of the apparatus can have any size, shape, and structure and be formed from any material not inconsistent with the objectives of the present invention. In some embodiments, for instance, the conduit is formed from a polymeric material such as a polyurethane, a polyester, a polycarbonate, or a polyolefin such as polyethylene or polypropylene, etc. Moreover, in some cases, the conduit has a substantially tubular or cylindrical shape. Such a tubular or cylindrical conduit, in some embodiments, has an inner diameter between about 100 μm and about 50 mm, between about 100 μm and about 10 mm, between about 1 mm and about 10 mm, between about 1 mm and about 5 mm, or between about 200 μm and about 500 μm. In some cases, the conduit has a diameter greater than about 50 mm or less than about 100 μm. Further, in some cases, a conduit described herein has a length between about 1 mm and about 200 mm, between about 5 mm and about 100 mm, between about 10 mm and about 30 mm, or between about 50 mm and about 150 mm.

Additionally, a conduit described herein can comprise or be formed from any material not inconsistent with the objectives of the present invention. In some embodiments, for instance, the conduit is formed from a polymeric material such as a polyurethane, a polyester, a polycarbonate, a polycaprolactone, a polylactic acid (PLA), a collagen, a polytetrafluoroethylene (PTFE), a polymethylmethacrylate (PMMA), an ethylene-vinylacetate copolymer (EVA), a polydimethylsiloxane (PDMS), a polyether polyurethane, a polyethyleneterephthalate (PET), a polysulfone (PS), a polyethyleneoxide (PEO) or polyethylene glycol (PEG), a polyethylene oxide-polypropylene oxide copolymer (PEO-PPO), a polyolefin such as polyethylene (PE) or polypropylene (PP), or a combination of one or more of the foregoing. In some instances, the conduit comprises a segment of implantation or catheter tubing, such as Micro-Renathane implantation tubing. Other materials may also be used.

Similarly, the microchannels of a conduit described herein can have any size and shape not inconsistent with the objectives of the present invention. In some cases, for instance, a substantially tubular or cylindrical microchannel has a diameter between about 100 nm and about 2000 μm, between about 100 nm and about 50 μm, between about 100 nm and about 1 μm, between about 500 nm and about 10 μm, between about 500 nm and about 5 μm, or between about 500 nm and about 1 μm. In some embodiments, the microchannels have an average diameter between about 100 μm and about 2000 μm, between about 100 μm and about 1000 μm, or between about 300 μm and about 800 μm. In some cases, the microchannels have an average diameter of less than about 100 μm or greater than about 2000 μm. Further, the microchannels can have a length up to about 99%, up to about 95%, up to about 90%, or up to about 80% of the length of the conduit of the apparatus.

Further, in some embodiments, the microchannels of an apparatus described herein are disposed within a matrix material disposed in the conduit. Any matrix material not inconsistent with the objectives of the present invention may be used. In some cases, for instance, a matrix material comprises a hydrogel, such as, for example, a biodegradable hydrogel. A "biodegradable" material, for reference purposes herein, comprises a material that can decompose within a biological environment, and may provide a non-toxic decomposition product. In some cases, a biodegradable material described herein comprises one or more ester bonds. In some instances, a matrix material of an apparatus described herein comprises an agaraose gel. Any agarose gel not inconsistent with the objectives of the present invention may be used. In some cases, for example, the matrix material comprises an agarose gel comprising between about 0.5 and about 5 weight percent agarose, between about 1 and about 4 weight percent agarose, or between about 1.5 and about 2.5 weight percent agarose, based on the total weight of the agarose gel. Additional non-limiting examples of matrix materials suitable for use in some embodiments of apparatuses described herein include polylactic-co-glycolic acid (PLGA), polylactic acid (PLA), polycaprolactone, polyurethane, polyester, polycarbonate, collagen, polytetrafluoroethylene (PTFE), polymethylmethacrylate (PMMA), an ethylene-vinylacetate copolymer (EVA), a polydimethylsiloxane (PDMS), polyether-polyurethane, a polyethyleneterephthalate (PET), a polysulfone (PS), a polyethyleneoxide (PEO) or polyethylene glycol (PEG), a polyethylene oxide-polypropylene oxide copolymer (PEO-PPO), a polyolefin such as polyethylene (PE) or polypropylene (PP), or a combination of one or more of the foregoing. Other matrix materials can also be used alone or in combination.

Moreover, any fiber not inconsistent with the objectives of the present invention can be coiled around the exterior of a microchannel described herein. A "fiber," for reference purposes herein, comprises any elongated structure such as, for example, a strand or filament. A fiber described herein can have any diameter not inconsistent with the objectives of the present invention. In some embodiments, for instance, a fiber described herein has a diameter (prior to being coiled or wrapped in manner described herein) between about 100 nm and about 100 μm, between about 500 nm and about 50 μm, between about 1 μm and about 50 μm, or between about 10 μm and about 50 μm. Additionally, in some embodiments, a coiled fiber comprises coils, loops, or turns having an outer diameter between about 10 μm and about 1000 μm, between about 50 μm and about 500 μm, or between about 100 μm and about 500 μm.

Referring to the preferred orientation of the fiber relative to the microchannel, it is understood that the fiber, in its preferred coiled state, preferably occupies the region defined by the outer circumference, or is otherwise oriented adjacent to the outer circumference, of the microchannel. In this way, as used herein, the term "exterior of the microchannel" refers to any orientation whereby the coiled fiber is positioned in concert with, or encircles the microchannel.

Further, in some variations, a fiber of an apparatus described herein comprises or is formed from a polymer such as a biodegradable polymer. In some cases, a fiber comprises or is formed from a poly(glycolide), poly(lactide), poly(glycolide-co-lactide), poly(p-dioxanone), alginate, polylactic-co-glycolic acid, a polylactic acid, a caprolactone, or a combination thereof. In addition, as described further hereinbelow, a fiber of an apparatus described herein can be coiled around the exterior of a microchannel of the apparatus in any manner not inconsistent with the objectives of the present invention. In some cases, for instance, the fiber is coiled around the exterior of the microchannel in an isotropic configuration. An "isotropic" configuration, for reference purposes herein, comprises a configuration having a uniform or substantially uniform pitch. The "pitch" of a fiber, for reference purposes herein, comprises the number of loops or coils of the fiber per length of the microchannel around which the fiber is coiled. A "uniform" pitch, for reference purposes herein, comprises a pitch that does not vary along the length of the microchannel. A "substantially" uniform pitch, for reference purposes herein, comprises a pitch that varies by less than about 10 percent, less than about 5 percent, or less than about 1 percent along the length of the microchannel. Alternatively, it is also possible for a fiber described herein to be coiled around the exterior of the microchannel in an anisotropic configuration. An "anisotropic" configuration, for reference purposes herein, comprises a non-istropic configuration, such as a non-isotropic configuration described further hereinbelow. Moreover, in some variations, a fiber described herein does not block or obstruct the microchannel of an apparatus described herein.

The active agent of a fiber described herein can comprise one or more active agents not inconsistent with the objectives of the present invention. An "active agent" for reference purposes herein, comprises a chemical species that can provide a chemical gradient in a manner described herein. For example, in some cases, an active agent comprises a drug, a peptide, a protein, a growth inhibiting factor, or a growth promoting factor such as a nerve growth factor (NGF). Thus, in some embodiments, the chemical gradient provided by an apparatus described herein comprises a drug concentration gradient or a growth factor concentration gradient. Any drug not inconsistent with the objectives of the present invention may be used. An active agent can also comprise other desired molecular signals or markers. Further, in some embodiments, the active agent is biologically active and/or non-denatured.

In addition, as described further hereinbelow, some embodiments of apparatuses described herein comprise a plurality of microchannels disposed in the conduit. The microchannels can have the same or differing sizes, shapes, and/or structures. Further, in some cases comprising a plurality of microchannels, a plurality of fibers can be coiled around the exteriors of one or more of the plurality of microchannels. In some instances, the plurality of fibers are each coiled around the exterior of a different microchannel and at least two of the coiled fibers comprise the same or differing active agents, the same or differing amounts of an active agent, and/or the same or differing pitches and/or dimensions.

In another aspect, compositions are described herein which, in some embodiments, can provide one or more advantages compared to some other compositions. For example, in some embodiments, a composition described herein provides one or more advantages also provided by an apparatus described herein. Moreover, a composition described herein, in some cases, can be used in addition to or instead of an apparatus described herein to form a chemical gradient.

A composition described herein, in some embodiments, comprises a coiled polymeric material comprising an active agent operable to diffuse out of the polymeric material when the polymeric material is disposed in a biological compartment. The coiled polymeric material, in some cases, can have the same structure as the fiber of an apparatus described herein. For example, in some cases, the coiled polymeric material of a composition described herein is biodegradable. In some embodiments, the polymeric material comprises a polylactic-co-glycolic acid, a polylactic acid, a caprolactone, or a combination thereof. Further, in some cases, the active agent comprises a drug or growth factor. Additionally, the biological compartment of a composition described herein can comprise any biological compartment not inconsistent with the objectives of the present invention. In some cases, for instance, the biological compartment comprises a portion of a living organism. Further, in some embodiments, the biological compartment comprises a nerve conduit. Other biological compartments may also be used, as described further herein.

In other variations, a composition described herein does not necessarily include a coiled component such as a coiled fiber or polymeric material described herein. In some cases, for instance, a composition described herein comprises a first gradient material or matrix comprising an active agent at a first concentration and a second gradient material or matrix comprising the active agent at a second concentration, wherein the first matrix and the second matrix are arranged in space to provide a concentration gradient of the active agent. The active agent can comprise any active agent described herein, such as a drug or growth factor. Moreover, in some variations, a composition described herein further comprises a third gradient material or matrix comprising the active agent at a third concentration, and the first matrix, second matrix, and third matrix are arranged in space, or oriented, to provide a gradient region comprising a concentration gradient of the active agent. The gradient region, in some cases, can comprise a linear concentration gradient. In addition, in some embodiments, the first, second, and third matrices of a composition described herein are arranged to provide a plurality of concentration gradients, including a plurality of linear concentration gradients. Moreover, in some cases, the first, second, and third matrices can be arranged to provide a non-gradient region in addition to a gradient region described herein. A gradient material or matrix of a composition described herein can comprise or be formed from any material not inconsistent with the objectives of the present invention. In some cases, for instance, a matrix is a gel that comprises or is formed from a polymeric material, including a biodegradable polymeric material. In some embodiments, a gel comprises a hydrogel. In some instances, a gel comprises or is formed from an agarose gel, a polylactic-co-glycolic acid, a polylactic acid, a caprolactone, or a combination thereof. Other gel or non-gel materials may also be used as matrices to establish the desired gradient(s).

Further, as described herein, a composition can be disposed in a conduit to provide an apparatus. Thus, in another aspect, apparatuses are described herein, wherein the apparatus comprises a conduit with a composition described herein disposed in the conduit.

In yet another aspect, methods of forming a chemical gradient are described herein, which, in some variations, may provide one or more advantages compared to some other methods. For example, in some cases, a method described herein can provide a chemical gradient in a modular and/or tunable manner. Additionally, in some instances, a method described herein can provide a chemical gradient exhibiting a sustained, non-transient chemical gradient in vivo. A method of forming a chemical gradient described herein, in some variations, comprises disposing an apparatus and/or a composition described herein in a biological compartment. In some cases, the chemical gradient comprises an active agent concentration gradient, such as a drug gradient or a growth factor gradient. Additionally, in some instances, the biological compartment comprises a nerve conduit. Further, any apparatus and/or composition described herein may be used in a method described herein.

Some embodiments described herein are further illustrated in the following non-limiting examples.

Example 1

Apparatus Comprising a Single Microchannel

Figure 1B:
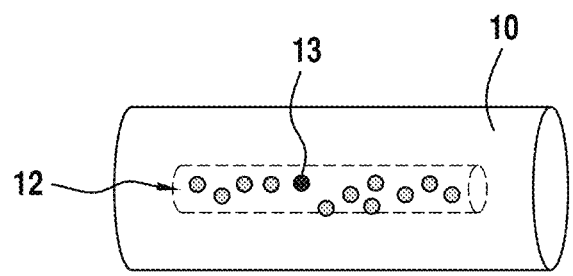
Figure 1C:
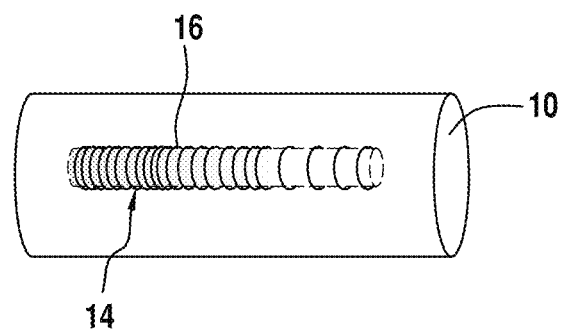
FIG. 1C illustrates a perspective view of an apparatus according to one embodiment described herein.

In one variation, an implantable device is fabricated that provides a chemical gradient and enables localized delivery of a specific growth factor within a microchannel through which axons will grow. For comparative purposes regarding this variation, FIG. 1A illustrates a lumen or microchannel 11 within a conduit 10. The microchannel 11 comprises an active agent (not shown) to provide at least a transient region of a desired chemical potential. However, active agent concentration over the microchannel length is difficult to control using the structure of FIG. 1A. As an additional comparative example for this variation, FIG. 1B shows a microchannel 12 within a conduit 11 comprising embedded microparticles 13. The microparticles 13 are impregnated with an active agent (not shown) such as drug or growth factor and can be biodegradable. The microparticles 13 can degrade or otherwise release the active agent predictably over time in a preselected or controlled, programmable fashion. Therefore, the structure of FIG. 1B can provide a concentration of active agent within the microchannel 12 over a period of time. However, this model lacks a concentration gradient. In contrast, FIG. 1C shows an embodiment of an apparatus according to the present disclosure. Coiled fiber 16 is impregnated with an active agent and surrounds a microchannel 14. The microchannel 14 is embedded within a hydrogel conduit 10. The positioning of the coils of fibers 16 along the length of microchannel 14 creates a controllable gradient of active agent that is released into the microchannel 14. The concentration, and thus a controllable gradient, can be predictably adjusted by changing the number of helical turns, pitch, or lateral distance between the turns, the dimensions or thickness of the fiber, and/or the length of the channel. Thus, the apparatus of FIG. 1C permits long-term active agent delivery by producing a sustained chemical gradient in the microchannel. The chemical gradient is provided through the release of active agents from the coiled fiber and into the microchannel by diffusion over time. The time profile of the release of active agents from the coiled fiber can be controlled based on one or more of: the concentration of the active agent within the fiber, the size and/or chemical composition of the active agent, the chemical composition and/or microstructure of the fiber material, and the chemical composition and/or microstructure any matrix material disposed in the conduit. Further, the number of turns of the fiber around the microchannel, in some embodiments, can be programmed to provide a desired steepness of a chemical gradient. The term "programmed," for reference purposes herein, is understood to mean any preselected and predetermined orientation of the coils of a fiber that can be controlled and is controllable to provide a desired result. The "steepness" of a chemical gradient, for reference purposes herein, comprises the slope of a plot of the concentration of a given active agent or other chemical species against the length of the microchannel in a given direction.

Example 2

Apparatus Comprising a Plurality of Microchannels

Apparatuses described herein, in some embodiments, comprise a plurality of microchannels. Such apparatuses can be used to stimulate the growth of axons across a gap. When axons must grow across a gap, there is often a need to separate specific modalities or types of axons into distinct compartments or spatial regions. Such a separation can be useful for the repair of sensory and motor branches and/or for the development of closed-loop peripheral neural interfaces. Moreover, such a separation can be achieved by disposing a plurality of fibers described herein around a plurality of microchannels of a device described herein, wherein the fibers differ in the amount and/or type of growth factor delivered to the different microchannels and/or differ in the steepness of the chemical gradient provided within the different microchannels. In this manner, a specific type of axon from a mixed population of nerves can be enticed into a specific microchannnel and thereby eventually guided to the proper target for the specific axon type. Further, this process can be carried out for a plurality of differing axon types in the mixed population.

Figure 2:
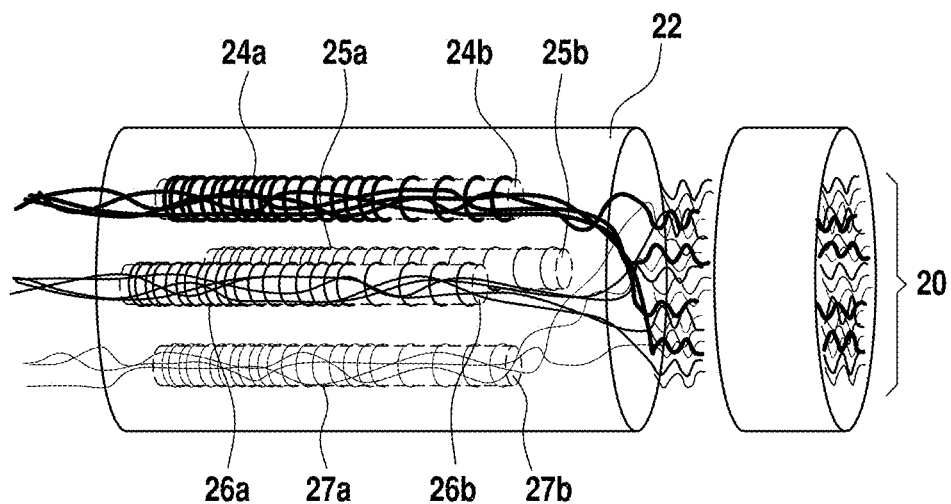
FIG. 2 illustrates a schematic perspective view of a mixed nerve population directing nerve cells into an apparatus according to one embodiment described herein.

FIG. 2 shows a schematic diagram of the application of several coiled fibers, preferably with differing gradients, in a multi-luminal conduit to guide axons and other cell types with different modality. This allows the guidance of different cell types to the conduit while providing each cell type's optimal concentration gradient. Modality-specific axonal guidance is one contemplated application of the establishment of the gradient. More specifically, FIG. 2 is a schematic diagram showing several axons 20 from a mixed nerve population guided into a multiluminal conduit 22 having coiled fibers 24a, 25a, 26a, 27a located in respective microchannels 24b, 25b, 26b, 27b, with each microchannel optionally able to have a different modality. In this variation, each lumen or micochannel is surrounded by a helically wound fiber that contains specific molecular cues (such as neurotrophin or pleiotrophin) known to entice growth of a specific type of neuron (nerve cells). Release of the molecular cues creates a gradient in the microchannels inside the coiled fibers. The gradient can be controlled by the fiber architecture as described further hereinabove (e.g., by selecting the total number of helical turns, the lateral distance between adjacent turns, and/or the pitch of the turns).

Figure 3:
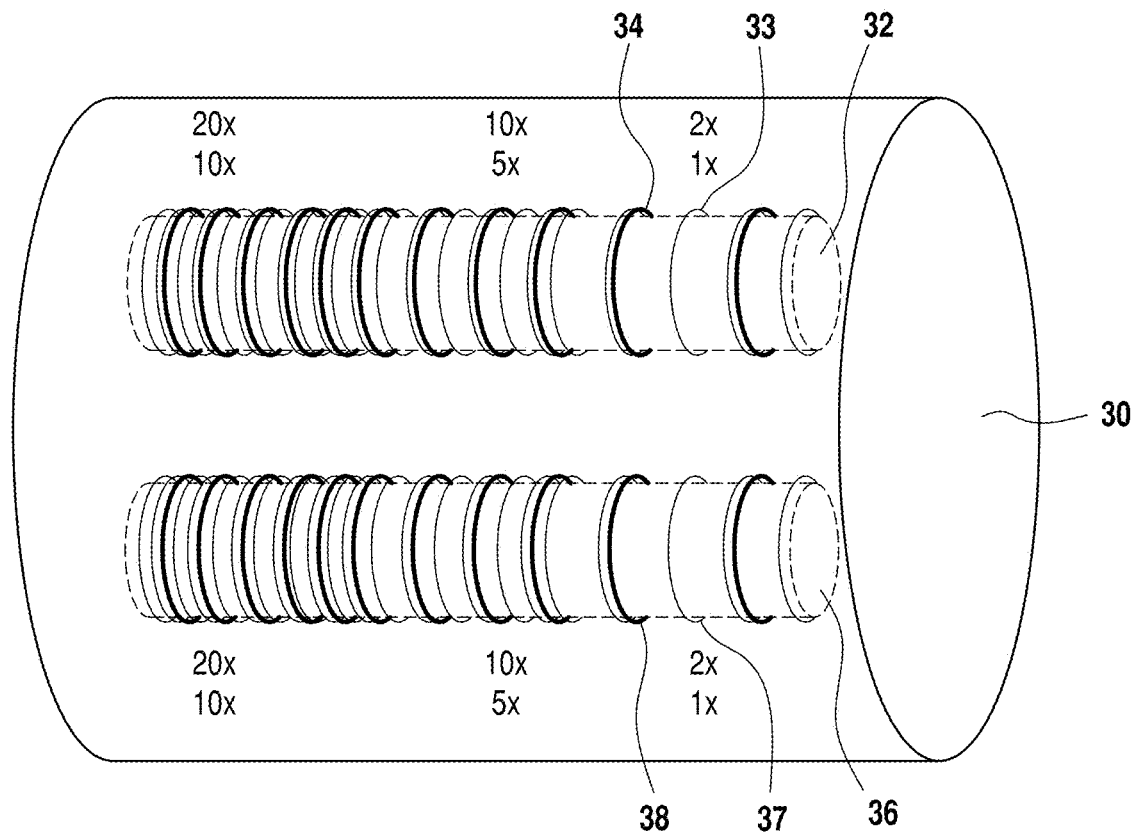
FIG. 3 illustrates a schematic perspective view of an apparatus according to one embodiment described herein.

To confirm the synergistic effects of multiple growth factors, the growth of the sensory neurons sprouted from single neurotrophic or pleiotrophic factors was tested. This testing determined a base-line of the growth induced by these chemical stimuli. FIG. 3 is a schematic diagram showing the application of multiple coiled fibers providing differing gradients in a multi-channel conduit to guide axons and other type of cells. As illustrated in FIG. 3, conduit 30 includes a first microchannel 32 having two coiled fibers 33, 34 oriented about the length of the microchannel wall. Similarly, a second microchannel 36 has two coiled fibers 37, 38 oriented about the length of the second microchannel wall. This structure permits the guidance of different cell types to different microchannels, where each microchannel can have a desired, preselected, and optimal concentration gradient of a particular active agent corresponding to a desired effect on the different cell types. For example, the differing chemical gradients of the differing microchannels can each be selected to promote growth of differing types of axons. It is to be understood that any number of active agents and any number of fibers may be disposed about a microchannel in any manner to achieve a desired chemical gradient.

Example 3

Method of Forming a Chemical Gradient

An apparatus having the general structure of the apparatus of FIG. 1C in Example 1 was used to form a chemical gradient according to one embodiment described herein as follows. First, a poly(DL-lactic-co-glycolic acid) (PLGA) coiled fiber was fabricated. The biodegradable PLGA (85: 15) co-polymer (0.84 intrinsic viscosity (i.v.), 135,000 weight average molecular weight (MW)) was fashioned into fibers using a wet-spinning process. Briefly, a solution 20 wt. % PLGA was completely dissolved in dichloromethane (Sigma-Aldrich, St. Louis, Mo.). This solution was loaded into a glass syringe (gas-tight, Hamilton, Reno, N.Y.) and injected into a 1.5-cm diameter tube filled with isopropanol to form the fiber. Pre-washed mylar substrates was used as collecting spools. With many spinning parameters possible, the spinning solution injection rate and the fiber collection speed were controlled at 1.8 mL/h and 8.5 m/min, respectively, to achieve 30 μm diameter fibers. In addition, if necessary, polyethylene glycol (PEG) was added to the spinning formulation to preserve the bioactivity of the active agent (such as a growth factor). To form coiled fibers, the fibers were wound around a glass rod (sometimes also called a formation fiber) and dried overnight to allow any remaining dichloromethane to evaporate. Following formation, the fibers were coiled around titanium fibers (diameter=250 μm) and stored at 4° C. prior to use.

To form fibers comprising an active agent (or a control species), the coiled fibers were disposed in a solution of the active agent overnight. For example, the following solutions were used to form PLGA fibers comprising an active agent (or a control species): (1) nerve growth agent NGF (5 μg/mL, Invitrogen, Carlsbad, Calif.); (2) control species bovine serum albumin (BSA, 20 mg/mL, Sigma-Aldrich, St. Louis, Mo.); and (3) fluorescent species cyanine dye-3 (Cy3, 5 μg/mL, Jackson ImmunoResearch Lab, West Grove, Pa.).

Figure 4A:
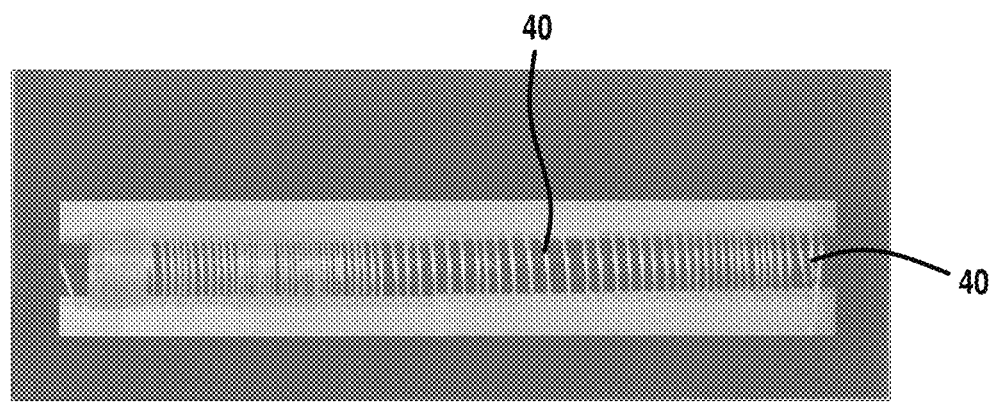
FIGS. 4A-F illustrate photographs of various components of an apparatus according to one embodiment described herein.
Figure 4B:
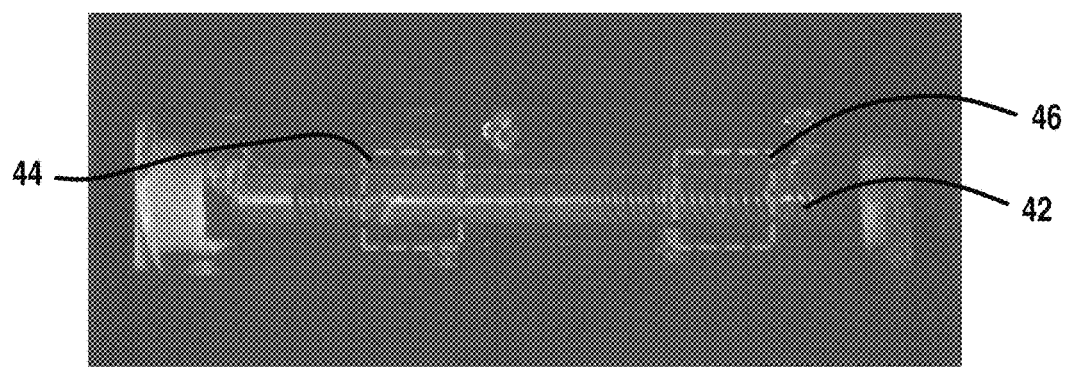
Figure 4C:
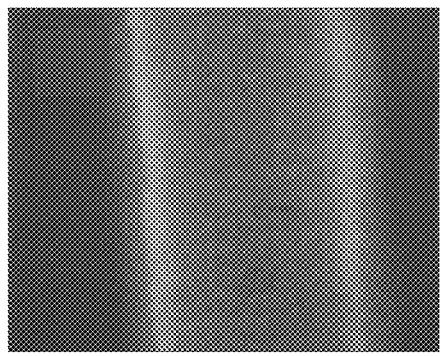
Figure 4D:
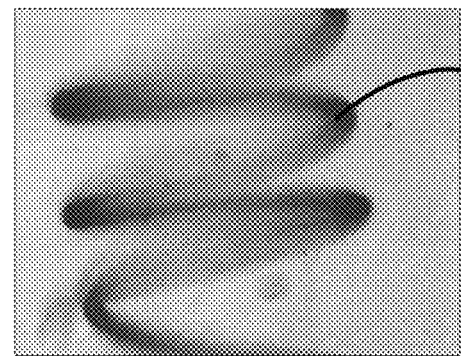
Figure 4E:
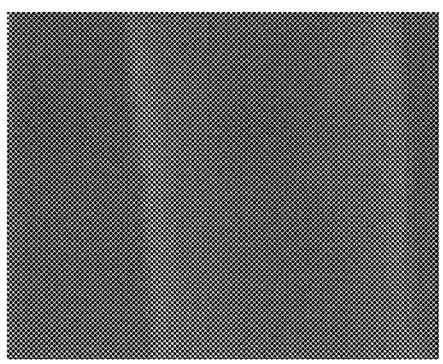
Figure 4F:
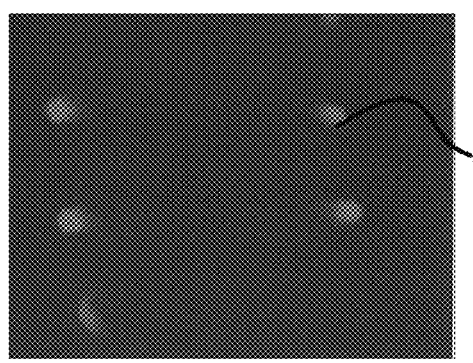

The Cy3-loaded PLGA coiled fibers were imaged using light microscopy and fluorescent microscopy to demonstrate that the coils provided a chemical gradient and tended to maintain their structures even after removing the fabrication metal. FIGS. 4A-F show magnified (microscope) images of the same fiber in the low and high concentrated areas, confirming the significant difference in the number of turns and the fluorescent light emanating from fibers loaded with fluorescent dye (Cy3). FIG. 4A shows an image of the wound coil 40 around a fabrication fiber (not shown). FIG. 4B shows the coiled PLGA fiber 42 that can be placed in a nerve conduit. FIGS. 4C-F are higher magnification images of the areas in boxes 44, 46 shown in FIG. 4B. The Cy3-PLGA coiled fiber 47 in FIG. 4D are imaged from the high density region, where "high density" refers to a relatively high pitch (Box 44). The Cy3-PLGA coiled fibers 48 are imaged from the low density region (Box 46).

Fabrication of the fibers requires harsh chemical procedures such as application of organic solvents (dichloromethane). To confirm that growth factors (proteins) were preserved throughout the process of the fabrication of the coils, NGF-loaded coiled fibers were provided in the presence of pheochromocytoma (PC-12) cells. PC-12 cells are a cell line that proliferate and differentiate in the presence of the nerve growth factor (NGF). Cells/ECM suspension were loaded into the cell well of the casting device area using a transparent multiluminal matrix (TMM) device described immediately below further hereinbelow, and were pushed into the lumen by creating a negative pressure. Cells seeded inside the lumen were fixed in 24 hours with 4% paraformaldehyde (PFA) and stained with Oregon Green Phalloidin and TO-PRO 3 Iodide (Invitrogen, Carlsbad, Calif.) to visualize the as cytoskeletal and nuclear labels, respectively. The PC-12 cells' processes lengths were measured in zero, low, and high concentration areas. To facilitate the penetration of staining dyes, the gels were placed in a cell culture plate while the solution was stirred over night at 4° C. using a magnetic plate and stir bar.

Pheochromocytoma cells (PC-12 cells) were loaded in a novel rectangular frame (12.5 mm×36 mm) used for casting agarose gels. The casting device was made of dental cement and used to guide multiple titanium fibers (0.25 mm×17 mm; SmaltParts, Logansport, Ind.), Titanium fibers wound with growth factor-containing polymer coils were positioned through perforations at both ends of the device. Under sterile conditions, the casting device was placed over a glass slide in a cell culture dish and a 1.5% ultrapure agarose (Sigma-Aldrich, St. Louis, Mo.) solution was applied to cover the fibers and allowed to polymerize. PC12 cells ($1 \times 10^6$ ml) were suspended in growth factor-reduced Matrigel (3.5 mg/mL, BD Biosciences, San Jose, Calif.). The negative pressure generated during removal of the titanium fibers from the solidified gel, drew the PC12 cells/ECM mix into the lumen of the casted hydrogel microchannels. The growth factor coiled fibers were intact in the lumen and in approximate contact of PC12 cells. The cell cultures were fed with RPMI-1640 medium (Sigma, St. Louis, Mo.) and kept in the incubator at 37° C. and 5% $CO_2$ for 72 hours.

For visualization of differentiated PC12 cells in the microchannels, the gels were fixed in 4% paraformaldehyde (PFA) and processed for immunefluorescence. After rinsing the gels with a blocking solution (0.1% Triton-PBS/1% normal serum), the samples were incubated with Oregon Green Phalloidin and TO-PRO 3 Iodide (Invitrogen, Carlsbad, Calif.) as cytoskeletal and nuclear labels, respectively. The staining was evaluated using a Zeiss confocal microscope (Zeiss Axioplan 2 LSM 510 META). The staining was evaluated and analyzed using regular and fluorescent microscopy and z-stack 3D image reconstruction of the microvascular network in the multi-lurninal hydrogels. Quantification of the length of PC-12 cells processes in 3 different coil densities (none, low and high) was achieved using the Axiovision LE software (CariZeiss, Axiocam, version 4.7.2) and Zeiss LSM Image Browser (version 4.2.0.12).

All data values were expressed as mean±standard error of the mean. The data was analyzed by parametric student-t test or by non-parametric student-t test followed by Mann Whitney post hoc evaluation using the Prism 4 software (GraphPad Software Inc). Values with $p \leq 0.05$ were considered to be statistically significant.

Figure 5A:
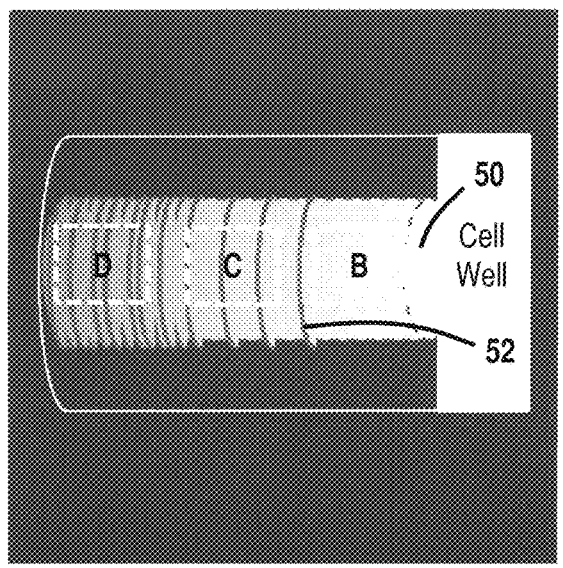
FIG. 5A illustrates a schematic perspective vie of an apparatus according to one embodiment described herein.
Figure 5B:
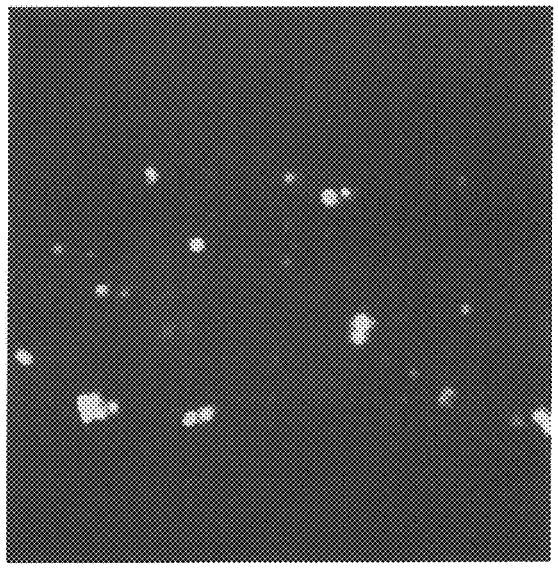
FIGS. 5B-D illustrate microscope images of a chemical gradient provided by the apparatus of FIG. 5A.
Figure 5C:
Figure 5D:
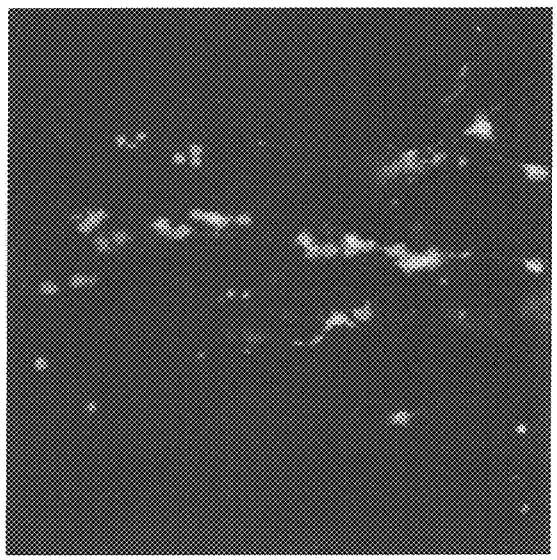

FIGS. 5A-D demonstrate the bioactivity of the PC-12 cells in NGF-loaded microchannels. FIG. 5A is a schematic diagram of the design of the experiment. An NGF-loaded coil fiber 52 was placed in a nerve conduit 50. PC-12 cells were then loaded inside the channel. FIG. 5B is a microscope image showing PC-12 cells located distally from the coil (the area in the microchannel corresponding to "Box B" in FIG. 5A). These cells did not show any processes 24 hours after being seeded. FIG. 5C is a microscope image showing PC-12 cells located in the middle of the coil (the area in the microchannel corresponding to "Box C" in FIG. 5A). These cells were differentiated and exhibited some processes in 24 hours. FIG. 5D is a microscope image showing PC-12 cells located in the high density area of the channels with the highest number of coil turns (the area in the microchannel corresponding to "Box D" in FIG. 5A). After 24 hours cells in this region were differentiated and exhibited long processes. Images of the cells inside the lumen looked spherical and showed no processes in the area where there was no NGF loaded coil. Howevers, cells seeded in the areas with NGF loaded coiled fibers were completely differentiated and had long processes. Interestingly, these processes were longer in the area with higher density of coil. This confirmed that areas with higher numbers of turns will release more NGF and therefore have higher concentration of the growth factor. To quantify the visualized images, the length of all the processes equal to or longer than the cell body was measured. The quantitative analysis of the data showed a significant difference between the lengths of the cell processes (see FIG. 6) in the three "boxed" areas B-D depicted in FIGS. 5B-D. P value equal to or less than 0.05 was considered significant. The average length of the processes was significantly higher in proximal (p<0.002; n=6; 71.33+/−12.17 μm) area and middle (35.66+/−12.69 μm) compared to distal (1.4+/−1.14 μm).

Figure 6:
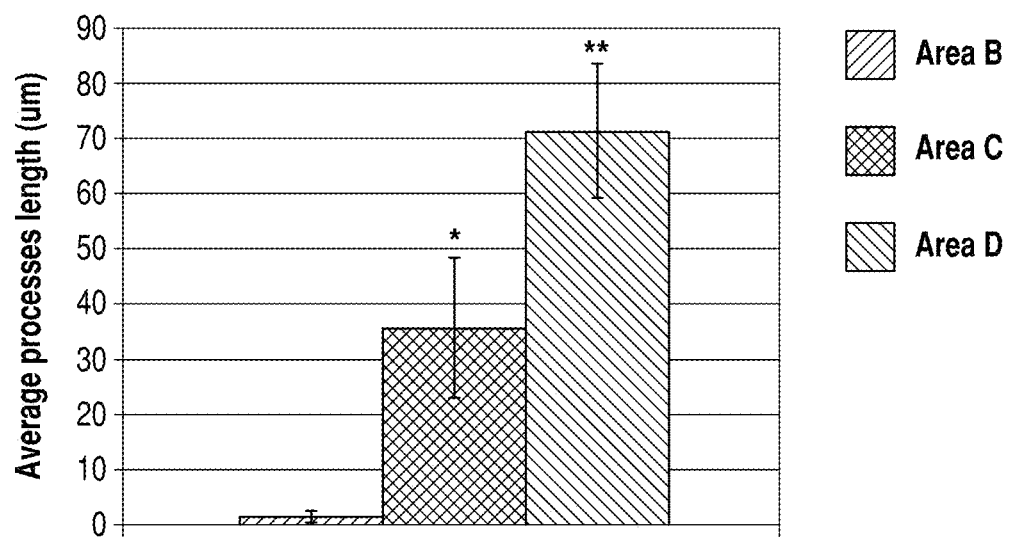
FIG. 6 illustrates a graph of the average cell process lengths corresponding to the chemical gradient of FIGS. 5B-D.

FIG. 6 charts the bioactivity of the PC12 cells in NGF loaded coiled fiber in the microchannel. NGF loaded coil fiber was placed in a nerve conduit. The bioactivity of the PC-12 cells was determined by measuring cells processes in the area without any NGF ("Box B" in FIG. 5A), the area with low density of coil turns ("Box C" in FIG. 5A) and the area with high density of coil turns ("Box D" in FIG. 5A). Cells were imaged 24 hours after seeding and processes length was measured using ImageJ. As shown in FIG. 6, PC12 cells loaded distally from the coil (Box B in FIG. 5A) did not show any processes 72 hours after being seeded. PC12 cells located in the middle of the coil (Box C in FIG. 5A) differentiated and had some processes in 24 hours. After 72 hours, PC12 cells located in the high density area of the channels with the most number of NGF loaded coil turns (Box D in image shown in FIG. 5A) were differentiated and had long processes. PC12 cells located in the middle of the coil (Box C in image FIG. 5A) differentiated and had some processes in 24 hours. There was a significant difference in the length of the cell processes in the different areas (*) p<0.05 and (**) p<0.005.

Example 4

Method of Forming a Chemical Gradient

Growth factor release from poly-lactic-co-glycolic acid (PLGA) coils was modeled in two configurations (isotropic and anisotropic) of a mu medium model solved using finite element analysis. The model was implemented in COMSOL Multi physics using a 2.4 GHz Intel® Core™2 Quad processor computer and consisted in rings with a diameter of 250 micrometers and thickness of 1 micrometer distributed inside a cylinder with a diameter of 250 micrometers and a length of 1 centimeter. The first configuration (isotropic) consisted of a uniform distribution of 20 rings. The second configuration (anisotropic) consisted of the arrangement of 3 sections with arrangement of rings at different distances from one another. The sections consisted of sections with 250, 500, and 1000 micrometers. The release profile from the loaded PLGA coils was modeled using a modified version of Korsmeyer-Peppas equation for the release from a degradable polymer. The initial condition of the coil was taken as a uniform load of 1 microgram. The simulations were run for a period of 28 days.

In the mathematical model the filling conduit was considered to have the diffusion coefficient of the agarose gel. The diameter of the channels was considered to be 250 µm. The results of the mathematical analysis showed that the isotropic coiled fiber created a homogenous concentration in the channels which w a s maintained for 28 days. Both ends of the conduit were considered to be open. Therefore, in the proximal and distal end, a decrease in the concentration of the growth factor was observed due to the diffusion flux out of the lumen. However, the change in the concentration of the proximal and distal ends compared to the middle was minimal (less than 15% of the concentration in the middle) and the conduit structure tends to preserve the homogenous concentration. The anisotropic configurations of the coiled fiber created a gradient as early as 5 days and tend to maintain the gradient for long time (at least 28 days), The out flux of the growth factor from the distal and proximal ends did not affect the establishment of the gradient. The steepness of the gradient was maintained substantially the same throughout the study (from day 5 to day 28). The mathematical speculation of the isotropic design of the coiled fiber was noted. The homogeneous distribution of the gradient in the isotropic design will remain for at least 28 days in the microchannels. Images of the predicted concentration distribution in the microchannels using Comsol confirmed the establishment of a sustained gradient at least for 28 days in the anisotropic configuration.

Example 5

Method of Forming a Chemical Gradient

Intraluminal NGF-Collagen Gradient Protocol

A method is described herein that achieves sustained growth factor release through the production of molecular gradients in collagen-filled multiluminal nerve guides, as shown in FIGS. 7A-G and FIGS. 8A-B. To achieve this, NGF-releasing fibers coiled onto titanium rods were inserted into openings made in a transparent multi-luminal matrix (TMM) casting device. The TMM consists of a square plastic open frame with holes at opposite ends through which the titanium rods are inserted. 1.5% agarose was subsequently added over the metal rods, effectively embedding the NGF-releasing polymeric coils in agarose.

Nerve guides (NG) incorporate NTF gradients in the tube wall (FIG. 7A) or use NTF-eluting microparticles (FIG. 7C). However, current multiluminal NG designs lack NTF release by a gradient. This study uses coiled polymeric fibers anchored to the walls of hydrogel microchannels with luminal collagen to address this limitation (FIG. 7D). FIG. 7E is a photograph of Cy3 IgG-loaded PLGA fibers coiled onto a metal rod. Fluorescence imaging and densitometry illustrate the resulting gradient. FIG. 7F is a schematic of the Transparent Multiluminal Matrix (TMM) casting device showing fiber coil deployment. Removal of the metal rod from the TMM after agarose polymerization anchors the coils onto the walls of the microchannels while simultaneously filling the lumen with collagen (FIG. 7Fi-iii). In FIG. 7G, confocal images show the deployed polymeric coils (red) with the collagen filler (green) in the TMM. Scale bar=100 um.

More specifically, as shown in FIG. 7A, collagen conduit 70a comprises NGF provided in a gradient. FIG. 7B shows a conduit 70b comprising multiluminals or microchannels 72b comprising NGF. FIG. 7C shows a conduit 70c comprising multiluminals or microchannels 72c comprising NGF microparticles 74. In this variation, the microchannels 72c each comprise a substantially uniform concentration of NGF. FIG. 7D shows a conduit 70d comprising multiluminals or microchannels 72d comprising NGF-loaded coil fiber 76 establishing a gradient.

According to a TMM method, collagen 77 was then added into the "loading" well of the TMM (FIG. 7Fi). Upon removal of the fiber forming metal (titanium) rod 78, the NGF-releasing fiber coil is retained at the walls of the resulting microchannels casted in agarose 79, and the negative pressure created by their removal substantially simultaneously fills the luminal space of such microchannels with collagen 77 (See FIGS. 9Fii-iii). This method is designed for the continued release of molecules such as Cy3-IgG, BSA or NGF encapsulated in the polymeric fibers into collagen-filled microchannels over time, providing both permissive and chemotactic nerve growth regulation. FIG. 7G is a microphotograph showing the coil 76 with the metal rod removed. FIGS. 7H and 7I are microphotographs of the coiled fiber 76 with collagen 77 introduced within the circumference of, and to "fill" the coiled fiber 76.

Growth Factor Releasing from Coiled Polymeric Fibers

Two fiber sources were used to fabricate 30 µm coiled fibers: poly-lactic-co-glycolic acid (PLGA 85:15; 135KD) and ELUTE™ Biodegradable Polydioxanone. PLGA fibers were fabricated by wet-spinning. Briefly, a 20% PLGA solution was prepared in dichloromethane (DCM; Sigma-Aldrich, St. Louis, Mo.), dispensed onto a circulating isopropanol coagulation bath using a syringe pump (1.8 mL/hr), collecting the resulting fiber onto a rotating spool (8.5 m/min). Dried PLGA coil fibers were incubated with NGF (10 µg/mL; Invitrogen, Carlsbad, Calif.), BSA (20 mg/mL; Sigma-Aldrich, St. Louis, Mo.) or cyanine dye-3 (Cy3; 5 µg/mL; Jackson ImmunoResearch Lab, Inc., West Grove, Pa.) overnight. Most studies used ELUTE™ Biodegradable Polydioxanone fibers, custom fabricated by TissueGen Inc, Dallas, Tex. to encapsulate NGF and coil it 80 times over titanium metal rods (0.25 mm×17 mm; Small-Parts, Logansport, Ind.) either equally (uniform) or differentially spaced at 15, 25, and 40 turns over 3.33 mm longitudinal area (10-100 ng/mL gradient). Fibers were dried at RT and stored at −20° C. until used.

Figure 8A:
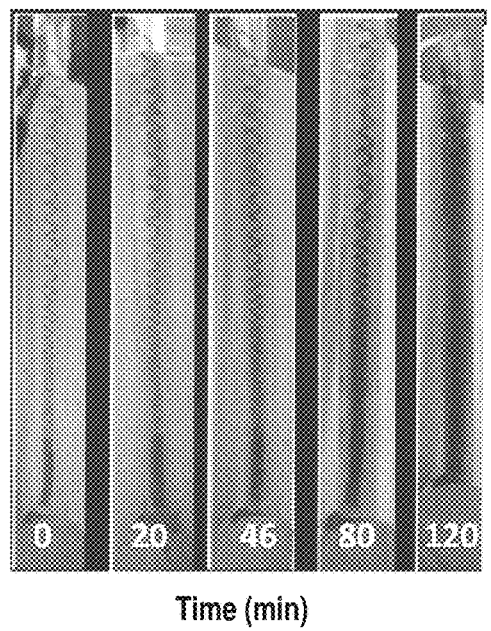
FIG. 8A illustrates a series of microscope images of chemical gradients formed according to some embodiments of methods described herein.
Figure 8B:
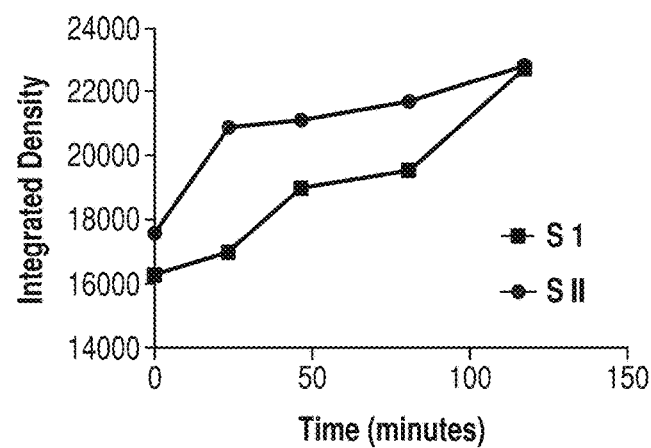
FIG. 8B illustrates a plot of the chemical gradients of FIG. 8A.

Conductive polymer polypyrole was loaded with red dye. As shown in FIG. 8A, upon electrical simulation, the dye was released over 120 minutes of time from the fiber and established a gradient. FIG. 8B shows the quantification of SI and SII areas, confirming the gradient formation.

PC12 Cell Culture

Figures 9A, 9B, 9C:
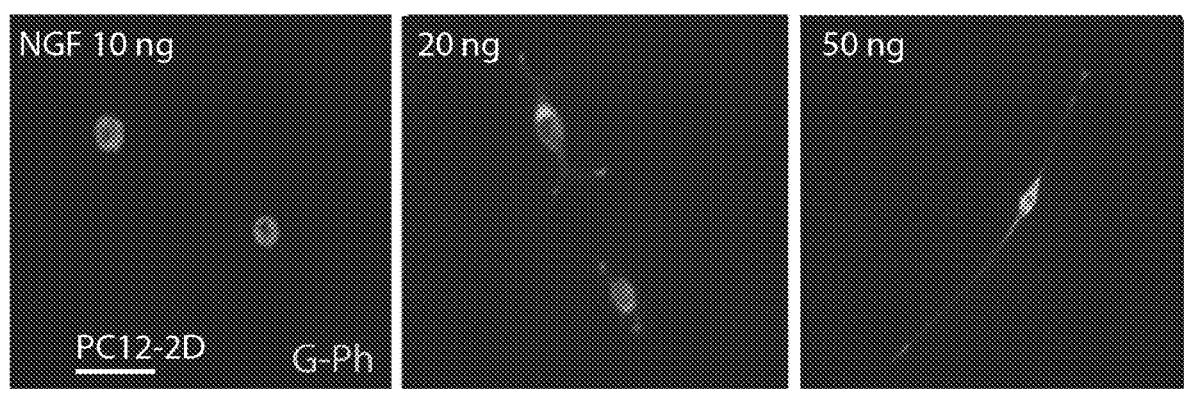
FIGS. 9A-C illustrate microscope images of nerve cells disposed in a chemical gradient according to one embodiment described herein.

Metal rods with coiled PLGA fibers containing either BSA or NGF were deployed in the TMM casting device as described above. Under sterile conditions, the casting device was placed over a glass slide in a cell culture dish and 1.5% ultrapure agarose was used to cover the fibers. After polymerization, Pheochromocytoma cells (PC12; 1×10$^6$/mL) suspended in atelomeric chicken collagen (85% type I, 15% type II; Millipore) were loaded onto the casted 250 µm OD hydrogel microchannels by the negative pressure generated. The TMM cell cultures were cultured for 72 hrs in RPMI-1640 medium (Hyclone SH30027.02) supplemented with 10% HS, 5% FBS, and 1% pen/strep and maintained at 37° C. and 5% $CO_2$. At the end of the study, the cell cultures were extensively rinsed with PBS and stained. Separate regular cultures of PC12 cells were cultured in normal dishes at a 1×10$^6$ plating density and exposed to a 10-100 ng/mL NGF range to determine their biological response (see FIGS. 9A-C). Using the PC12 as biosensors, the neurite response to different NGF concentrations was measured. Linear regression was used to define an equation to calculate the luminal concentration of NGF in the TMM microchannels based on the PC12 neurite length. The PC12 cells were shown to respond to variable levels of NGF. As shown in FIG. 9A-C, the neurite lengths of differentiated cells increase as the level of NGF concentration increases (as indicated in confocal images). FIG. 9A shows a NGF concentration of 10 ng/mL. FIG. 9B shows a NGF concentration of 20 ng/mL. FIG. 9C shows a NGF concentration of 50 ng/mL (scale bar=100 µm).

Growth Factor Diffusion Modeling

Growth factor release from PLGA coils was modeled in both uniform and gradient configurations considering the multi-medium environment (i.e., agarose microchannels with luminal collagen) using finite element analysis. Protein release kinetics were estimated by using fitting release data provided by the manufacturer into a power law equation. The power law equation with geometry (K=0.37), time (t=0-28 d), and release mechanism (n=0.25; $(M_r=M_\infty K^n)$ where M is the amount of drug released and $M_\infty$ is the total amount of drug). Release kinetics from PLGA coils were estimated using the bulk-eroding model considering an initial burst followed by diffusion via interconnected pores. The Carman-Kozeny model was used to estimate molecular diffusion (D) in water, 1.5% agarose, and 0.3% collagen considering molecular concentration ($\Phi$) changes over time ($\delta t$) in a fixed volume ($\Omega$). Diffusion flux vectors (J=D$\nabla$41)) integrated perpendicular to the surface (S) by the following formula: $\delta\chi/\delta t)\nabla\Phi=\Sigma J*n\nabla S$ released from the polymeric fibers. The model was implemented in Multiphysics Modeling and Engineering Simulation Software (COMSOL 4.0) considering the external tube (T) as a solid cylinder with a 3 mm OD, 1.5 mm ID and 10 mm length, and agarose michrochannels. The meshing module used included tetrahedral, triangular, and hexahedral mesh volume elements for the boundaries with maximum element size of 180-1000 µm, element size, 1.5 growth rates and a curvature resolution of 0.6. The model was validated using published exact solutions, and incorporated release kinetic data obtained in vitro.

DRG Explant Growth in Mill Microchannels

Neonate (P0-4) DRG cells were isolated from normal mice and placed at one end of the TMM microchannels containing either uniform or gradient NGF-coils. The DRG cultures were cultured in Neurobasal A media (Sigma, St. Louis, Mo.) and maintained at 37° C. and 5% $CO_2$ for 7 days prior to fixing them in 4% PFA by immersion. Afterwards, the cultures were rinsed and stained.

Immunostaining

TMM gels were extensively rinsed in PBS. The PC12 cells were then reacted with Oregon Green Phalloidin to label cytoskeletal. For immunolabeling of DRG axonal growth, the tissue was incubated in 4% Donkey serum for 1 hour, followed by incubation with a mouse anti-β tubulin III antibody (1:400; Sigma Aldrich) overnight at 4° C. The tissue was then incubated with Cy2-conjugated donkey anti mouse IgG (1:400; Sigma Aldrich) and rinsed. Long-working distance water immersion objectives on a Zeissconfocal microscope (Zeiss Axioplan 2 LSM 510 META) were used to evaluate the cellular staining and axonal growth directly within the hydrogel microchannels.

Image Analysis and Quantification

Neurite length in differentiated PC12 cells was evaluated inside the microchannels at low concentration (SI) and high concentration (SII) areas (FIGS. 10A-K) corresponding to different numbers of NGF coils. Neurite length was measured from the cell body to the distal end of the neurites. Only cells with neurites longer than the cell diameter are considered for quantification, using Axiovision LE software (CarlZeiss, Axiocam, version 4.7.2), Zeiss LSM Image Browser (version 4.2.0.1). The axonal length of the DRG was quantified at 20× magnification from a z-stack (20 images each at 308 µm slice thickness). Axonal length was measured from the edge of the DRG to the growth cone terminal using Axiovision LE software (CarlZeiss, Axiocam, version 4.7.2) and Zeiss LSM Image Browser (version 4.2.0.1) for segments with no coils and medium (1-8) or high (9-15) number of coils in that segment. The turning angles of the axons were measured using Image J. Quantification of the turning angle was calculated as a ratio of all the axons present to the number of axons that turned. All experiments were done in duplicate 3-6 times each.

Statistical Analysis

All data values were expressed as mean±standard error of the mean. The PC12 data was analyzed by a parametric student t-test followed by Mann Whitney post hoc evaluation. The data obtained from the DRG experiments were evaluated by ANOVA followed by Newman-Keuls Multiple Comparison using the Prism 4 software (GraphPad Software Inc.). Values with p≤0.05 were considered to be statistically significant.

Results

PC12 Differentiation in a 3D NGF Microgradient

Figure 10J:
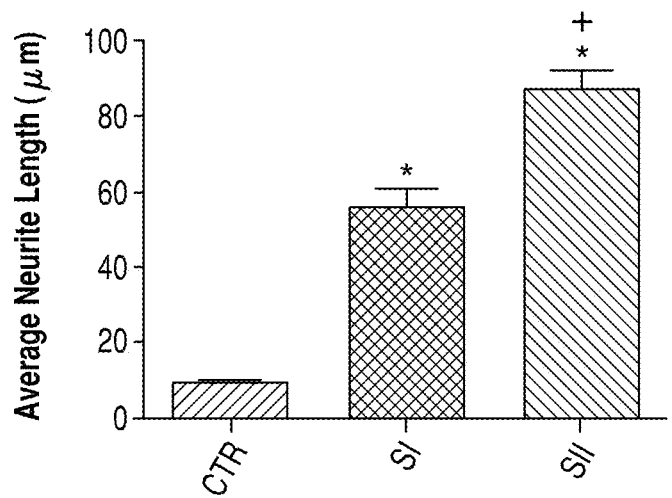
FIG. 10J illustrates a graph corresponding to FIGS. 10A-I.

To determine if the polymeric coils can be used to establish biologically active gradients of neural growth factors, the ability of PC12 cells to differentiate in the lumen of the TMM microchannels onto which BSA or NGF-eluting coils were anchored to the hydrogel walls was tested. Three days after seeding, only rounded undifferentiated cells were observed in the BSA controls (see FIGS. 10A-C). In contrast, those cultured with NGF-coils showed several degrees of neural differentiation as indicated by neurites elongating from the PC12 cell bodies. Neurite extension was observed to be proportional to the number of coils placed in the channels. Those with low number of coils (segment I; SI) showed a mixed population of round undifferentiated cells and some with neurites (FIGS. 10D-F), but those in areas of higher number of coils (segment II; SII) were mostly differentiated cells, with apparently longer neuron-like extensions (FIGS. 10G-I). To confirm this observation, the neurite length in differentiated PC12 cells in both areas was estimated, which revealed a significantly larger number of differentiated PC12 cells in the SII region (87±14.6 µm) compared to that in the SI area (55.76±12.53 µm; p<0.005). Both of these were, in turn, significantly different from that observed in BSA-releasing coils (9.31±1.94 µm; p<0.0001.) See FIGS. 10J and 10K.

Figure 10K:
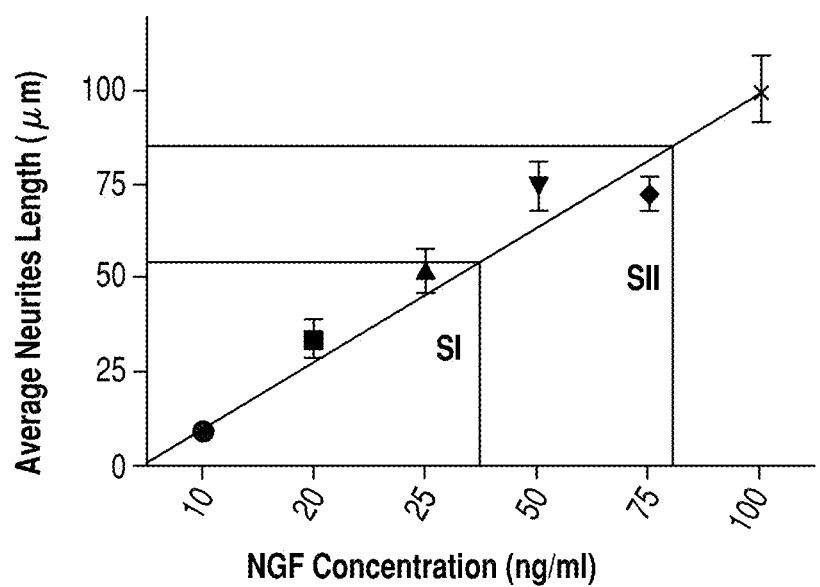
FIG. 10K illustrates a calibration curve corresponding to FIGS. 10A-J.

DIC and florescent images of PC12 cells cultured in collagen-filled agarose microchannels in which a BSA (FIGS. 10A-C; control) or NGF (FIGS. 10D-I) releasing fibers were coiled over the wall. The PC12 remain undifferentiated in the CTR group (arrowheads), but extend in those releasing NGF (arrows) and were more abundant in areas under higher number of coils (SII) when compared to areas with lower number of coils (SI). FIG. 10J shows the quantification of neurite length of differentiated PC12. FIG. 10K shows the calibration curve of neurite length of PC12 cells exposed to variable levels of NGF. The superimposed linear regression shows NGF concentration values corresponding to low (SI) and high (SII) number of fiber coils in the microchannels. *=p<0.0001 compared to CTR; +=p<0.005 compared to SI (n=6).

Figure 11:
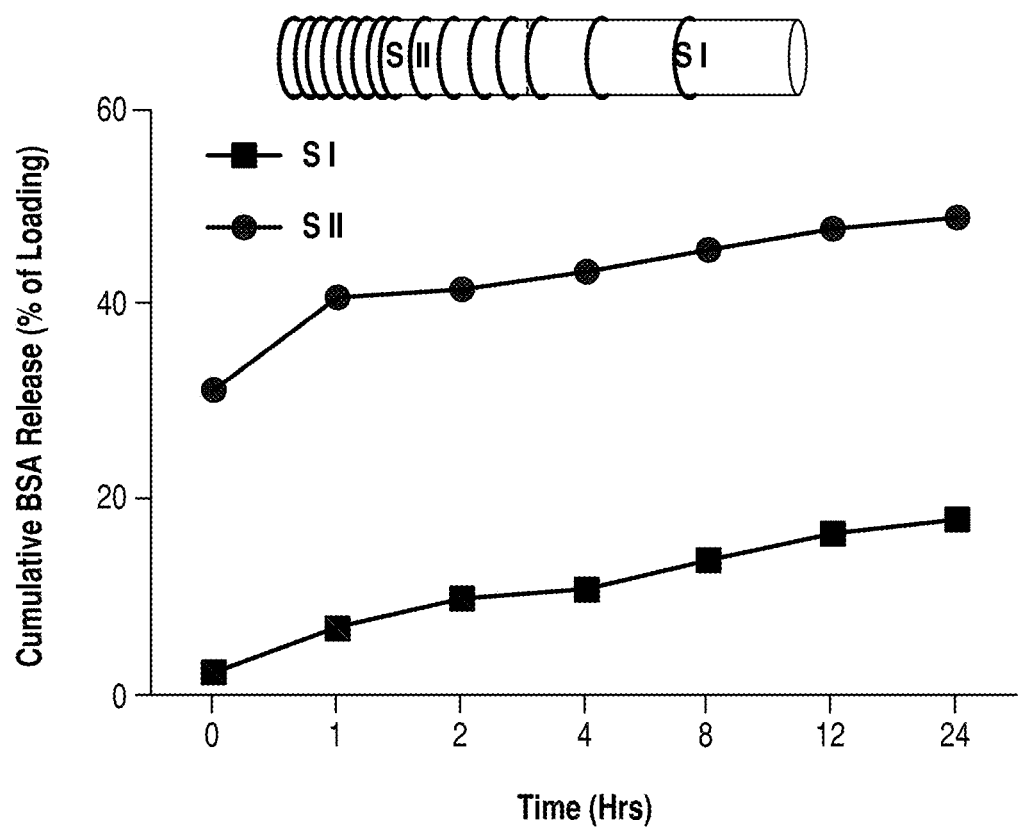
FIG. 11 illustrates a graph of the release profiles of a molecule according to some embodiments of chemical gradients described herein.

These observations indicated that the polymeric coils were able to release biologically active NGF into the luminal collagen matrix, forming a gradient at which low (SI) and high (SII) concentrations areas can be established. This notion was supported by quantification of protein release from the SI and SII regions of coils eluting ELISA BSA-releasing coils placed in the TMM agarose microchannels over 24 hrs, confirming a differential concentration of 50% less in the SI area compared to that in SII (See FIG. 11). The concentration of biologically active NGF in the SI and SII microchannel areas in situ was then directly evaluated by using PC12 as biosensors, as it is known that their differentiation is linearly proportional to the NGF concentration. The neurite length of PC12 exposed to a NGF 10-100 ng/mL concentration range was determined. It was further determined that these cells extended from 5 to 120 µm in length, linearly correlating to the NGF concentration (R=0.96; see FIG. 10K). A linear regression equation estimated from the PC12 growth calibration curve was then used to determine the intraluminal NGF (NGF=[(PC12 neurite length+1.91)/(17.06)]). Using this formula it was determined that the growth observed at low (SI) and moderate (SII) coiling regions of the TMM microchannels corresponded to 40 and 83 ng/mL of NGF; respectively, which is in close agreement with the observed differences with protein release. Quantification of BSA release from the TMM microchannels shows 40% of encapsulated BSA was released from segment II, compared to 20% release in SI after 24 hours.

Modeling of Protein Microgradient Diffusion

Next, a computer model was designed to predict the kinetics of NGF diffusion on the luminal collagen filler of the TMM microchannels. A computer simulation model in COMSOL was implemented that incorporated the diffusion coefficient values of proteins of similar size to NGF from the polymer fiber to the microchannel lumen, both in agarose and in collagen, over a 10 mm longitudinal distance according to the actual physical dimensions of the TMM gel. It was estimated that the NGF concentration in the microchannel volume (0.7 µl) over 1, 5 and 7 days, and compared those with uniform (U) and gradient (G) coil distribution patterns on their wall surfaces. As protein diffusion coefficient through luminal 0.1% collagen (7.6-12 $m^2$/sec) is faster than that through the 1.5% agarose microchannel structure (2.31-14 $m^2$/sec), diffusion occurs primarily through the collagen axis. According to the model, at 7 days, polymeric fibers in the U coil configuration form an even concentration along the microchannel at approximately 7 ng/mL, that dilutes out close to the proximal and distal openings. In contrast, the G coil configuration results in a linear gradient ranging from 0.02-12.42 ng/mL towards the end with a higher number of coils and also dilutes out near the ends. In addition to the expected concentration differences, the model predicted changes over time that appear significant between the two configurations. The U configuration remains stable over time with increasingly larger dilution zone at the end of the channels.

However, G deployment of the coils results in extension of the gradient from the higher to the lower concentration over time. Despite the dilution effect at the end of the microchannel, the steepness of the gradient in the G configuration does not seem to change significantly during the simulation period, providing a 0.02-12 ng/mL gradient at average 30 degree steepness (see FIG. 12).

Figure 12:
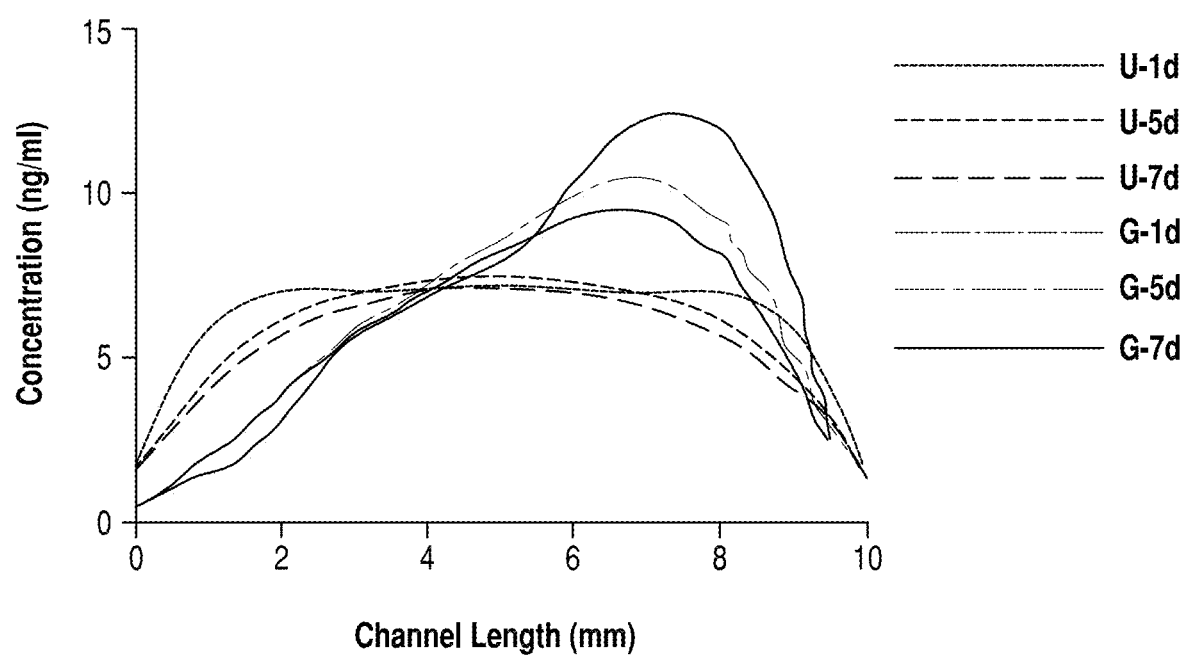
FIG. 12 illustrates a graph of the release profiles of a molecule according to some embodiments of chemical gradients described herein.

The uniform distribution of the coils results in even diffusion of NGF across the microchannel over 1-7 days with some dilution at the ends. The differential deployment of coiled fibers results in a 10-100 ng/mL NGF concentration gradient with a steep angle of 22 degrees, which increases and expands over time to cover most of the volume of the microchannel. As shown in FIG. 12, this difference is accentuated when the uniform and gradient concentrations are compared along the longitudinal axis.

Together, the results confirmed that greater numbers of coiled fibers on the walls of the agarose microchannels were able to establish linear molecular gradients of biologically active growth factors in the luminal collagen matrix that can then be used to chemotactically guide axonal growth.

Nerve Growth is Enhanced and Directed by 3D Gradient Growth Factor Delivery

Figure 13A:
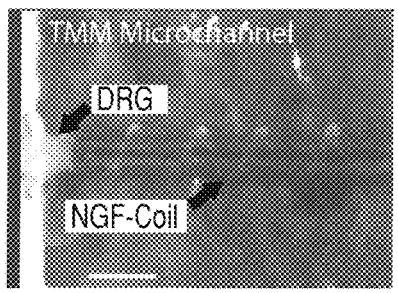
FIGS. 13A-D illustrate microscope images of nerve cells disposed in chemical gradients according to some embodiments described herein.
Figure 13B:
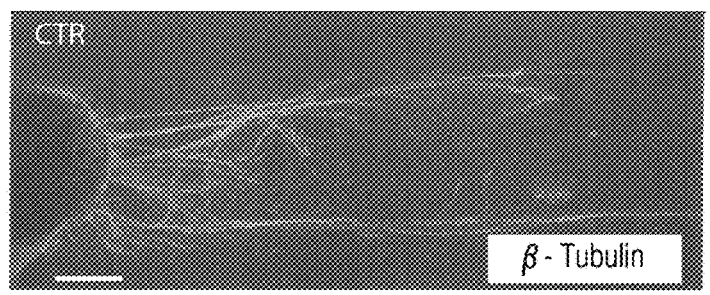
Figure 13C:
Figure 13D:
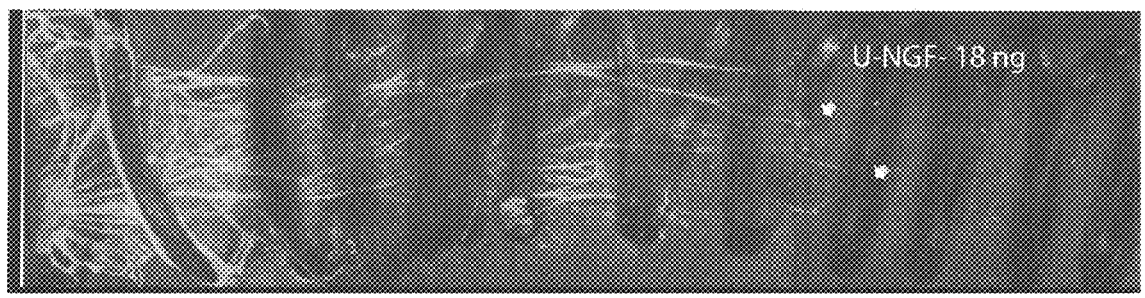
Figure 13E:
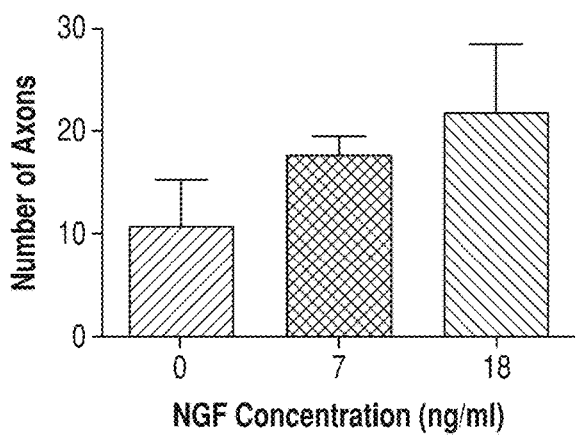
FIGS. 13E-F illustrate graphs corresponding to FIGS. 13A-D.
Figure 13F:
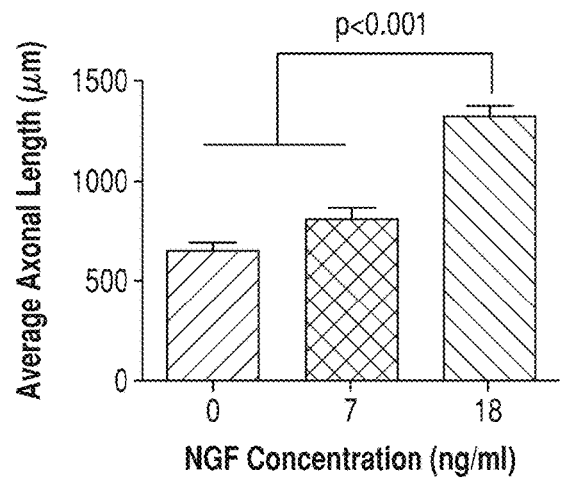

After confirming that the polymeric coils decorating the wall of the hydrogel microchannels can produce a sustaining growth factor gradient, the effect of NGF-eluting coils on nerve regeneration in vitro was tested by evaluating the number of axon fibers that extended from neonatal DRG placed at one end of the TMM gel (FIGS. 13A-F). Gels with no coils (FIG. 13B) were compared to those with uniform 7 turns and 14 turns of NGF ecapsualted coil. The extent of axonal growth was qualitatively better in the gels with NGF coils in comparison to the negative controls, although the increase in the number of axons did not reach statistical difference. However, quantification of the axonal length increased significantly ($p<0.005$; n=4) in the denser NGF coil group (1321±51.71 µm; 9-15 coil turns) compared to both the no growth factor (651.2±40.40 µm) and the low density coil groups (808.18±55.57 µm; <8 turns; FIGS. 13E-F). To confirm the beneficial effect of NGF gradients on sensory neuron regeneration, a separate group of DRGs was exposed to either uniform or gradient conditions in which the NGF concentration was maintained constant at 18 ng/mL.

FIG. 13A, shows differential intensity contrast (DIC) images of the TMM gel showing one casted microchannel filled with collagen and after placing a DRG explant at one end of the lumen. The PDO fiber coil is anchored into the agarose and onto the walls of the microchannel, filled with air for visualization. Confocal images of the of DRGs axonal growth immunolabeled for β-tubulin visualization (green) is shown for TMM gels with: no coils (see FIG. 13B); less than 9 turns of the NGF loaded fibers (see FIG. 13C); and 9-15 turns of the NGF eluting coils (see FIG. 13D). Quantification is shown for both: the Number of axons (see FIG. 13 E); and the axonal length of DRG (see FIG. 13F). The axonal length was measured using Zeiss LSM Image Browser (version 4.2.0.12). There was a significant difference in the length of the cell processes in the different areas (*<0.001).

Figure 14A:
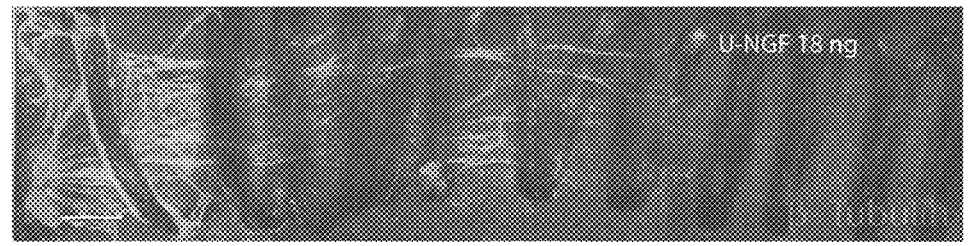
FIGS. 14A-B illustrate microscope images of nerve cells disposed in chemical gradients according to some embodiments described herein.
Figure 14B:
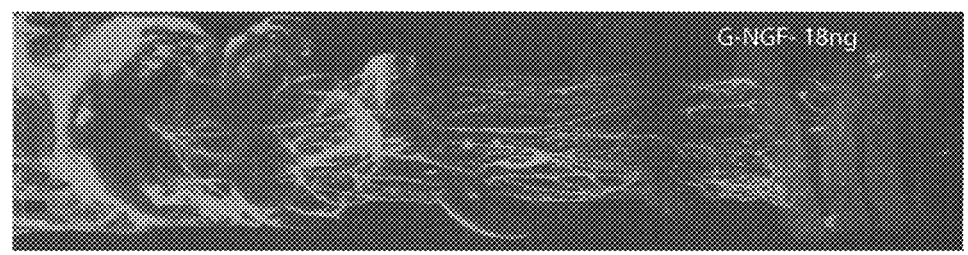
Figure 14C:
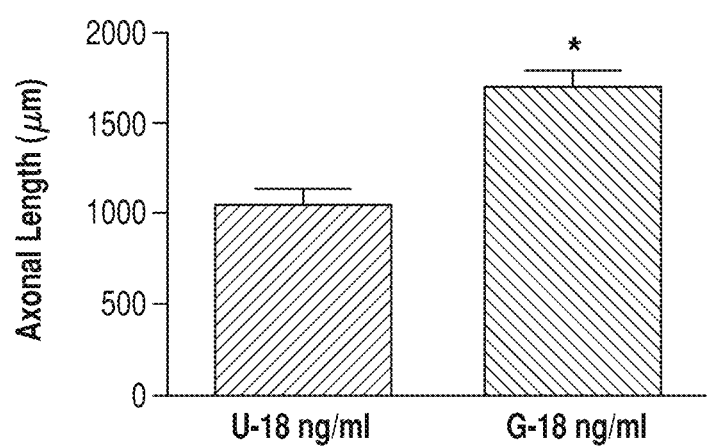
FIG. 14C illustrate a graph corresponding to FIGS. 14A-B.

To confirm the beneficial effect of NGF gradients on sensory neuron regeneration, a separate group of DRGs were exposed to either uniform (U) or gradient (G) conditions in which the NGF concentration was maintained at 18 ng/mL. Compared to the uniform concentration group (U) (FIG. 14A), those with coils arranged to establish a gradient (G) showed a more robust axonal regeneration (FIG. 14B). Quantification of the axonal length confirmed that a significant growth advantage ($p<0.05$) of neurons growing through cylindrical, collagen filled pathways supplemented with gradient NGF (1694±100.1; n=3), compared to those containing uniform growth factor concentration (1045±81.33, n=5; see FIG. 14C). Direct comparison of the axonal length observed in microchannels of DRG stained for β-tubulin (green) under uniform or gradient NGF conditions, while maintaining the same concentration, showed a significant increase in the axonal length of neurons growing towards an increasing NGF concentration. *$p<0.001$, n=3-5. Scale bar=100 µm.

Robust Axonal Chemotaxis towards NGF Gradients

Figure 15A:
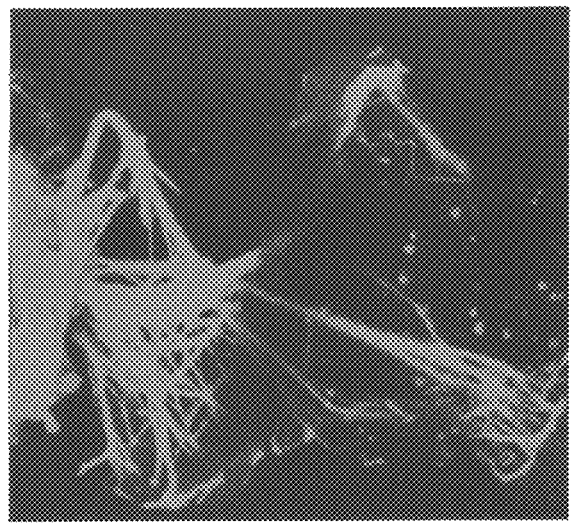
FIGS. 15A-B illustrate microscope images of nerve cells disposed in chemical gradients according to some embodiments described herein.
Figure 15B:
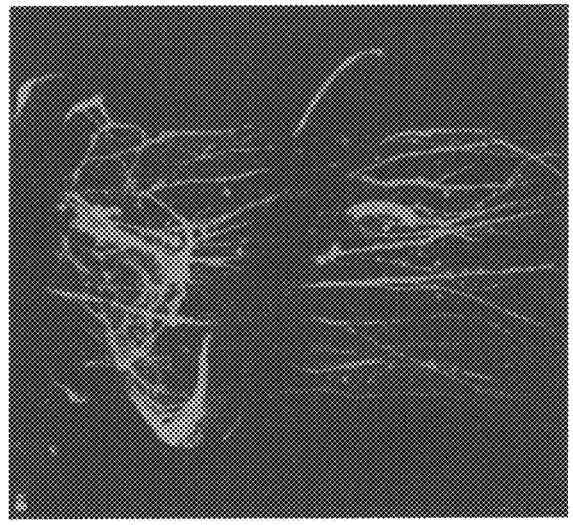
Figure 15C:
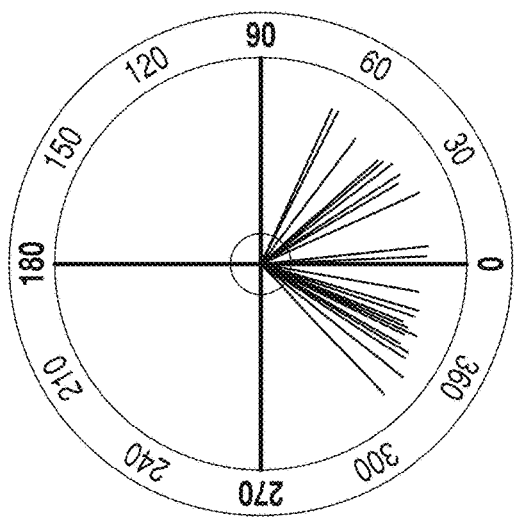
FIGS. 15C-D illustrate graphs corresponding to FIGS. 15A-B.
Figure 15D:
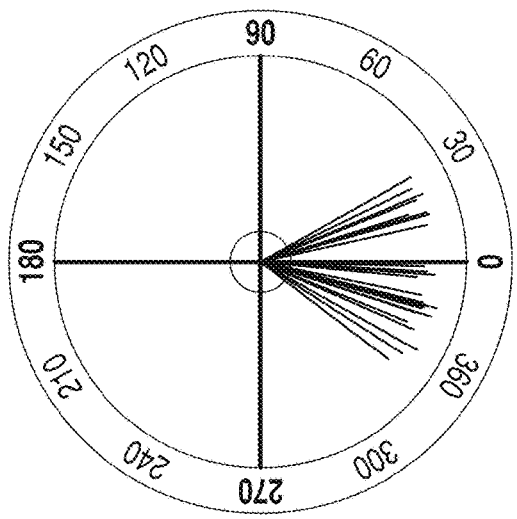

In addition to the growth-promoting effect of gradient NGF in DRG axonal elongation, it was noted that neurite elongation in the uniform groups was directed towards the coils on the walls of the microchannels. Indeed, axons in those groups were observed to follow upward and downward trajectories as they grew through the collagen (FIG. 15A). In sharp contrast, groups in which the NGF gradient was established towards the distal end, showed a robust linear growth, with axons ignoring the coils as they elongate (FIG. 15B). Quantification of the growth angle supported this notion as those in the uniform groups showed a broad directional growth ranging from +60 to −60° (FIG. 15C). Conversely, those presented with a gradient of NGF showed more directed growth angles, ranging from +30 to −30° (FIG. 15D).

β-tubulin labeled DRG axons were cultured and allowed to grow through a uniform distribution of the coils. The axonal growth was oriented toward the NGF loaded coils. See FIGS. 15 A and C. However, as shown in FIGS. 15B and 15D through a gradient distribution, the axonal growth tends to grow in the middle of the channel.

Figure 16:
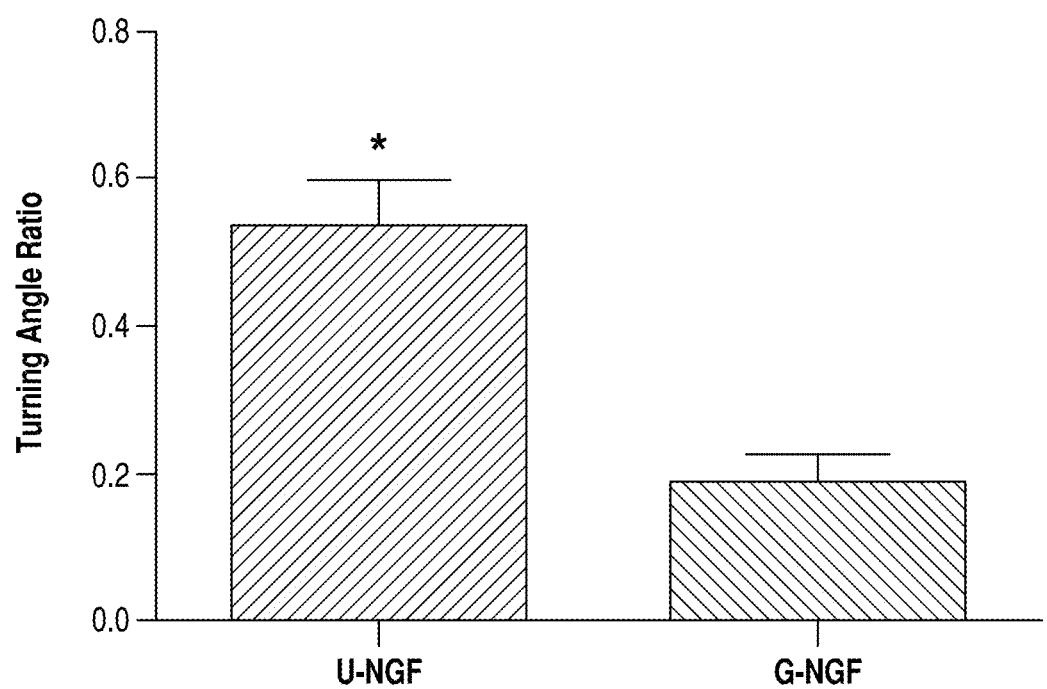
FIG. 16 illustrates a graph of turning angle ratio of axonal growth according to one embodiment of a method described herein.

The turning angle ratio of the axonal growth shows sharp, acute angles. Quantification of the turning angle was determined as a ratio of all the axon present to the number of the axon that turned. There was a significant difference in the turning ratio when uniform and gradient distribution were compared (*$p<0.005$). To further confirm this observation, the turning angle ratio was measured and determined that the number of axons that made sharp turns were significantly larger in the uniform group compared to those growing towards the NGF gradient ($0.5368 \pm 0.06321$, n=4; $0.1909 \pm 0.03772$, n=3; $p<0.005$) respectively. FIG. 16 shows the comparative observed turning angle ratio of DRGs exposed to either uniform (U) or gradient (G) NGF conditions. Together, this data shows that a strong chemotactic growth environment can be achieved through the release of growth factors into luminal collagen using a gradient of coiled polymeric fibers.

Further, target cells secrete growth factors forming molecular gradients that serve as chemotactic guidance cues for developing and adult injured neurons during axonal elongation and target recognition. During active path finding, axons sense gradients of attractive and repulsive molecules, which they use to orient their growth.

According to the present disclosure, and as stated above, a reproducible in vivo method was devised for anchoring protein loaded fibers, preferably polymeric fibers, into the wall of multiluminal hydrogel conduits, such as, for example, nerve conduits. The apparatuses, methods and compositions disclosed herein provide an intraluminal gradient without any obstruction to the regenerating axons. In addition, the present designs are highly tunable by varying the number of coil turns in each area to provide the proper gradient steepness.

Cells in living body migrate, differentiate and proliferate in response to diverse gradients of stimuli. The gradient can be physical or chemical in nature. Physical gradients include, for example, a gradual change in physical properties, such as surface topology, stiffness, and material porosity. For instance, in bone the pore size decreases from outside to inside. This phenomenon allows the mechanical properties to change as well as the gradient feature to allow cell migration and differentiation. Chemical gradients, especially those gradients of biological molecules, are also very important in all cell processes. For instance, cell migration not only depends on the absolute concentration, but also on the slope of the gradient. It has also been noted that the speed of the migrated cells was much faster when gradient and uniform surface are compared. Factors such as bFGF have been immobilized in a gradient orientation on a hydrogel to investigate the effect of this gradient on arotic smooth muscle cells. It is known that these cell align and migrate in the direction of the increasing gradient. Theoretical analysis has been used to predict the migration speed of cells over uniform and gradient substrate. Such models predict the relationship between speed and gradient to be biphasic dependent.

According to one variation, presently disclosed models allow the evaluation of the system performance and gives insight into the mechanism affecting dosage and release of the gradient. Despite all efforts to re-establish the gradient, most of these current technologies pertain to planer surface, ignoring that the three dimensional matrices are more closely mimicking the situation in vivo. Variations of the present disclosure provide methods to establish the gradient in 3D and can incorporate multiple gradient cues, and can be predictably, selectively, and controllably tuned based on the cell type.

According to the present disclosure, a bioactive concentration gradient of NGF has been established. The gradient of NGF can be controlled by varying the number of turns of the coiled fiber over a selected area. More specifically, PC12 responded to the concentration of NGF by extending neurites in a manner similar to that seen in soluble NGF. In addition, DRG growth and orientation were also influenced by the presence of the gradients. The gradient methodology described herein allows the encapsulation of any protein to target the cell of interest. The present disclosure contemplates the use of the disclosed apparatuses, methods and compositions with regard to either long gap repair in peripheral nervous system or axonal guidance in the injured spinal cord.

The repeatable and programmable gradient-formation methods disclosed herein have the capacity to deliver consistently more biological active agents to a desitred site, such as, for example, into a nerve regeneration site for the purpose of guiding axonal growth. The gradient concentration can be controlled by the number of turns (i.e., pitch) of the bio-fiber, either conducting or non-conducting, containing the active agent. The methods, apparatuses, and compositions disclosed herein can also be incorporated into implantable apparatus for releasing biological active agents in a time-controlled or quality-controlled manner though diffusion or electrical stimulation.

Therefore, the controlled gradient of the active agents (e.g. chemicals or biological substances, etc.) disclosed herein, can be applied in enticing and guiding nerve regeneration such as, for example, artificial choclear electrodes, in which the controlled delivery of substances such as brain-derived growth factor (BDNF) can be beneficial to attract neurons to the electrode and to preserve cell viability. Drug delivery of agents, where the concentration gradient is critical for biological effect, can also be carried out. This method is replicable and established gradients can be predictably achieved.

Figure 17:
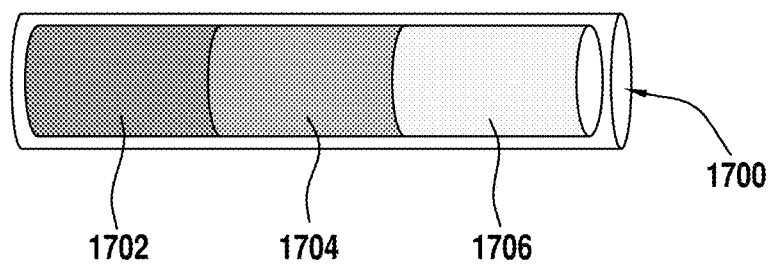
FIG. 17 illustrates a schematic perspective view of a composition according to one embodiment described herein.

More specifically, in some variations, a plurality or sequences of gradient materials or matrices, such as, for example, gels, etc. are stacked or otherwise arranged to provide a gradient. The gradient materials comprise different concentrations of a therapeutic agent and thus can provide a therapeutic gradient. The gradient materials can have any combination of therapeutic or other properties (such as physical properties) not inconsistent with the objectives of the present invention and can be used to model and/or recreate a variety of natural environments, including biological environments. In addition, any number of gels can be used. FIG. 17 shows a conduit 1700 comprising three gradient material sections 1702, 1704 and 1706, each having differing concentrations of a therapeutic agent, and arranged to form a gradient. However, it is also possible to use other numbers of gradient materials, such as, for example, two, four, five, or six gradient materials. In some cases, more than six gradient materials can be used. As shown in FIG. 17, gradient material section 1702 has the highest concentration; section 1704 is less concentrated; and section 1706 is least concentrated.

Figure 18:
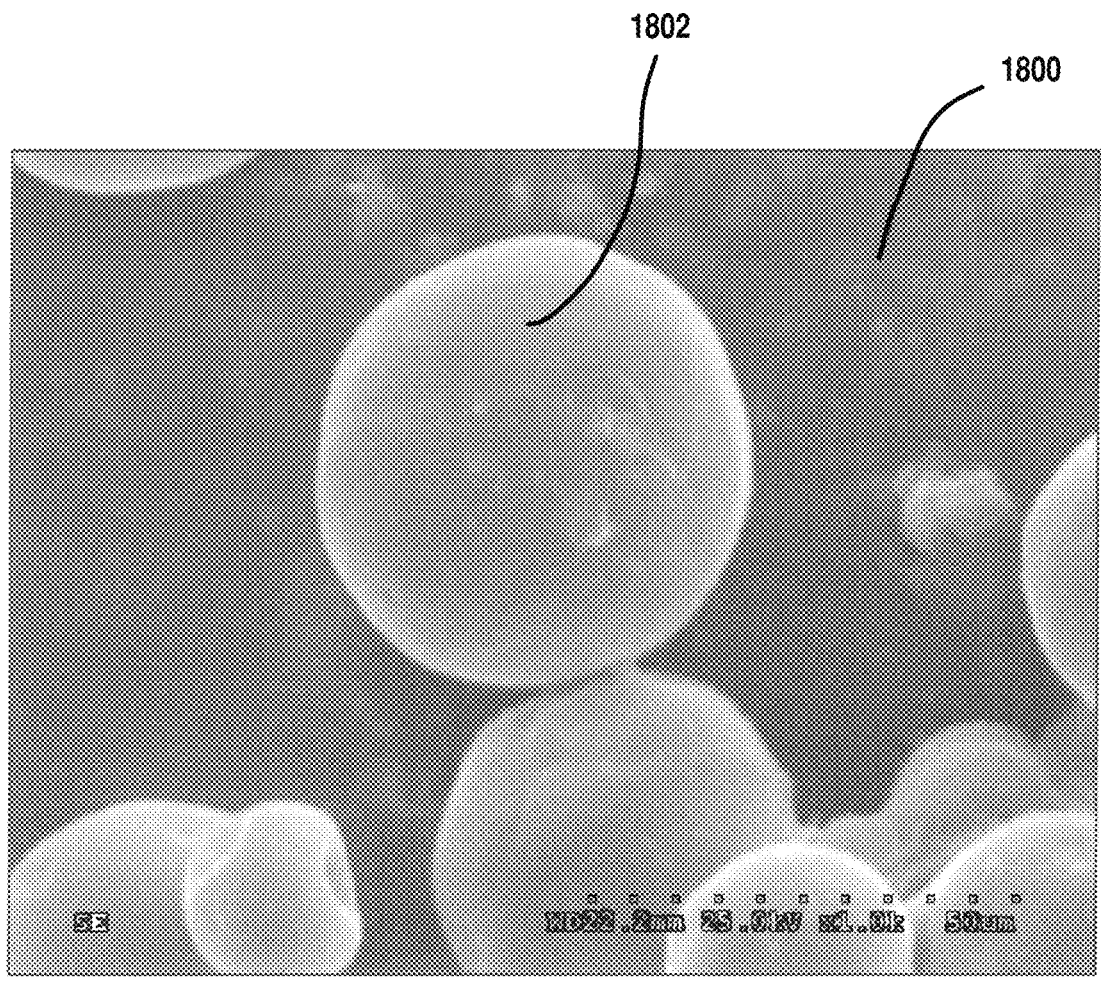
FIG. 18 illustrates a scanning electron microscope (SEM) image of a composition according to one embodiment described herein.

In addition, methods of forming a gradient using a soft, biocompatible component are also contemplated. These methods can be modified in various manners to achieve various objectives. In addition, as described herein, encapsulation of various factors can be achieved by the inclusion of various microparticle carriers to form a gradient. Contemplated variations include microparticles that are incorporated/suspended into a gel (e.g. a hydrogel, etc.) to provide a therapeutic gradient. FIG. 18 illustrates a scanning electron microscope (SEM) image of a composition according to one variation, where microparticies 1802 are shown suspended in a carrier matrix 1802, such as, for example, a gel such as a hydrogel.

Moreover, in some variations, a plurality of gradient materials or matrices, such as, for example, gels comprising active agents, such as, for example, therapeutic agents with each material preferably comprising a varying concentration of one active agent, multiple active agents, or varying concentrations of multiple active agents, can be arranged in an orientation to provide a preselected, predetermined and predictable gradient region and, if desired, a non-gradient region.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A composition comprising:
   a first matrix comprising an active agent at a first concentration; and
   a second matrix comprising the active agent at a second concentration differing from the first concentration,
   wherein the first matrix and the second matrix are arranged in space to provide a concentration gradient of the active agent,
   wherein the concentration gradient is a linear concentration gradient extending along a length of the composition, wherein the first matrix and second matrix are disposed in a conduit, and
   wherein the first matrix and/or the second matrix is formed from a hydrogel.

2. The composition of claim 1 further comprising a third matrix comprising the active agent at a third concentration.

3. The composition of claim 2, wherein the first, second, and third matrices define a non-gradient region and a gradient region.

4. The composition of claim 1, wherein the active agent comprises a drug, a peptide, a protein, growth inhibiting factor, a growth promoting factor, or a combination thereof.

5. The composition of claim 1, wherein the active agent comprises a nerve growth factor ("NGF") or a brain-derived growth factor ("BDNF").

6. The composition of claim 1, wherein the active agent in the first matrix is the same as the active agent in the second matrix.

7. The composition of claim 1, wherein the active agent in the first matrix is different from the active agent in the second matrix.

8. The composition of claim 1, wherein the active agent in each matrix comprises two or more active agents.

9. The composition of claim 1, wherein the first matrix comprises a first material and the second matrix comprises a second material.

10. The composition of claim 9, wherein the first material is the same as the second material.

11. The composition of claim 9, wherein the first material is the same as the second material.

12. The composition of claim 9, wherein the first material and/or the second material comprise an agarose gel, a polylactic-co-glycolic acid, a polylactic acid, a caprolactone, or a combination thereof.

13. The composition of claim 9, wherein the first material and/or the second material comprise an agarose gel comprising between 1.5 percent and 2.5 percent agarose.

* * * * *